(12) United States Patent
Wilson et al.

(10) Patent No.: US 8,590,555 B2
(45) Date of Patent: *Nov. 26, 2013

(54) LOW PRESSURE MEASUREMENT DEVICES IN HIGH PRESSURE ENVIRONMENTS

(75) Inventors: Robert F. Wilson, Roseville, MN (US); Douglas J. Duchon, Chanhassen, MN (US); Mark Gabbard, Sicklerville, NJ (US); Khader Mohiuddin, Medina, MN (US); Thomas J. McPeak, Shakopee, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 353 days.

This patent is subject to a terminal disclaimer.

(21) Appl. No.: 13/014,524

(22) Filed: Jan. 26, 2011

(65) Prior Publication Data

US 2011/0114197 A1    May 19, 2011

Related U.S. Application Data

(63) Continuation of application No. 12/575,199, filed on Oct. 7, 2009, now Pat. No. 7,905,246, which is a continuation of application No. 11/401,695, filed on Apr. 10, 2006, now Pat. No. 7,617,837, which is a continuation of application No. 10/316,147, filed on Dec. 9, 2002, now Pat. No. 7,389,788.

(60) Provisional application No. 60/338,859, filed on Dec. 7, 2001, provisional application No. 60/338,883, filed on Dec. 7, 2001.

(51) Int. Cl.
*G05D 11/00* (2006.01)

(52) U.S. Cl.
USPC .......... 137/1; 137/112; 137/843; 137/512.15; 137/605

(58) Field of Classification Search
USPC ......... 137/112, 113, 512.15, 512.4, 859, 605, 137/843, 1; 251/331
See application file for complete search history.

(56) References Cited

U.S. PATENT DOCUMENTS 3,065,761 A   11/1962 Peras
3,084,707 A   4/1963 Frye
(Continued)

FOREIGN PATENT DOCUMENTS

GB       311974 A    5/1929
JP       53108637 S   8/1978
(Continued)

OTHER PUBLICATIONS

Communication from Canadian associate to the Canadian Patent Office regarding a reply to the Official Action dated Jan. 21, 2011 from the Canadian Patent Office for Canadian Patent Application No. 2,469,545, dated Jul. 18, 2011, 11 pgs.

(Continued)

*Primary Examiner* — Kevin Lee
(74) *Attorney, Agent, or Firm* — Shumaker & Sieffert, P.A.

(57) ABSTRACT

The present invention presents various novel approaches to solving the problems inherent in measuring biological pressures in high pressure systems. Thus, to protect a pressure transducer exposed to fluid flows at higher pressures than its overpressure rating, a novel valve is used that closes a protected leg in which the transducer is located. The various exemplary embodiments of such valves each have a high pressure input, one or more low pressure inputs, and an output. In operation, when a high pressure fluid flow occurs at a high pressure input, such valves automatically close the low pressure inputs. Alternatively, a novel transducer system is presented, which automatically limits the effective pressure sensed by a transducer to a certain maximum.

23 Claims, 37 Drawing Sheets

(56) References Cited

U.S. PATENT DOCUMENTS

| | | | |
|---|---|---|---|
| 3,092,130 A | 6/1963 | Hewitt |
| 3,157,201 A | 11/1964 | Littmann |
| 3,196,890 A | 7/1965 | Brandenburg |
| 3,245,426 A | 4/1966 | Kreuter et al. |
| 3,369,496 A | 2/1968 | Bushmeyer |
| 3,416,567 A | 12/1968 | Von Dardel et al. |
| 3,610,228 A | 10/1971 | Temkin |
| 3,633,605 A | 1/1972 | Smith |
| 3,731,679 A | 5/1973 | Wilhelmson et al. |
| 3,739,943 A | 6/1973 | Wilhelmson et al. |
| 4,084,606 A | 4/1978 | Mittleman |
| 4,243,031 A | 1/1981 | Genese |
| 4,252,116 A | 2/1981 | Genese et al. |
| 4,355,653 A | 10/1982 | Credle, Jr. |
| 4,457,330 A | 7/1984 | Fields |
| 4,457,487 A | 7/1984 | Steigerwald |
| 4,461,313 A | 7/1984 | Beaumont |
| 4,462,409 A | 7/1984 | Pace et al. |
| 4,506,691 A | 3/1985 | Tseo |
| 4,512,764 A | 4/1985 | Wunsch |
| 4,677,980 A | 7/1987 | Reilly et al. |
| 4,724,830 A | 2/1988 | Fischell |
| 4,819,684 A | 4/1989 | Zaugg et al. |
| 4,854,324 A | 8/1989 | Hirschman et al. |
| 4,858,127 A | 8/1989 | Fron et al. |
| 4,953,584 A | 9/1990 | Vegso |
| 4,966,579 A | 10/1990 | Polsachegg |
| 5,002,528 A | 3/1991 | Palestrant |
| 5,097,841 A | 3/1992 | Moriuchi et al. |
| 5,105,820 A | 4/1992 | Moriuchi et al. |
| 5,176,658 A | 1/1993 | Ranford |
| 5,188,603 A * | 2/1993 | Vaillancourt | 604/131 |
| 5,232,434 A | 8/1993 | Inagaki et al. |
| 5,236,417 A | 8/1993 | Wallis |
| 5,254,101 A | 10/1993 | Trombley, III |
| 5,356,375 A | 10/1994 | Higley |
| 5,460,609 A | 10/1995 | O'Donnell |
| 5,515,851 A | 5/1996 | Goldstein |
| 5,569,181 A | 10/1996 | Heilman et al. |
| 5,573,515 A | 11/1996 | Wilson et al. |
| 5,665,074 A * | 9/1997 | Kelly | 137/512 |
| 5,739,508 A | 4/1998 | Uber, III |
| 5,795,333 A | 8/1998 | Reilly et al. |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,840,026 A | 11/1998 | Uber, III et al. |
| 5,843,037 A | 12/1998 | Uber, III |
| 5,843,044 A | 12/1998 | Moorehead |
| 5,873,861 A | 2/1999 | Hitchins et al. |
| 5,885,216 A | 3/1999 | Evans, III et al. |
| 5,916,165 A | 6/1999 | Duchon et al. |
| 5,920,054 A | 7/1999 | Uber, III |
| 5,935,083 A | 8/1999 | Williams |
| 5,947,935 A | 9/1999 | Rhinehart et al. |
| RE36,648 E | 4/2000 | Uber, III et al. |
| 6,085,773 A | 7/2000 | Karg et al. |
| 6,096,011 A | 8/2000 | Trombley, III et al. |
| 6,099,511 A | 8/2000 | Devos et al. |
| 6,149,627 A | 11/2000 | Uber, III |
| 6,182,698 B1 | 2/2001 | Barak |
| 6,197,000 B1 | 3/2001 | Reilly et al. |
| 6,290,682 B1 | 9/2001 | Myers |
| 6,306,117 B1 | 10/2001 | Uber, III |
| 6,317,623 B1 | 11/2001 | Griffiths et al. |
| 6,318,403 B1 | 11/2001 | Fritz |
| 6,339,718 B1 | 1/2002 | Zatezalo et al. |
| RE37,602 E | 3/2002 | Uber, III et al. |
| 6,371,942 B1 | 4/2002 | Schwartz et al. |
| 6,385,483 B1 | 5/2002 | Uber, III et al. |
| 6,397,098 B1 | 5/2002 | Uber, III et al. |
| 6,402,717 B1 | 6/2002 | Reilly et al. |
| 6,440,107 B1 | 8/2002 | Trombley, III et al. |
| 6,442,418 B1 | 8/2002 | Evans, III et al. |
| 6,471,674 B1 | 10/2002 | Emig et al. |
| 6,475,192 B1 | 11/2002 | Reilly et al. |
| 6,520,930 B2 | 2/2003 | Critchlow et al. |
| 6,527,698 B1 | 3/2003 | Kung et al. |
| 6,569,117 B1 | 5/2003 | Ziv et al. |
| 6,638,258 B2 | 10/2003 | Schwartz et al. |
| 6,643,537 B1 | 11/2003 | Zatezalo et al. |
| 6,673,033 B1 | 1/2004 | Sciulli et al. |
| 6,699,219 B2 | 3/2004 | Emig et al. |
| 6,708,714 B1 | 3/2004 | Mijers |
| 6,731,971 B2 | 5/2004 | Evans, III et al. |
| 6,733,477 B2 | 5/2004 | Cowan et al. |
| 6,733,478 B2 | 5/2004 | Reilly et al. |
| 6,743,202 B2 | 6/2004 | Hirschman et al. |
| 6,866,654 B2 | 3/2005 | Callan et al. |
| 6,889,074 B2 | 5/2005 | Uber, III et al. |
| 6,896,002 B2 | 5/2005 | Hart et al. |
| 6,901,283 B2 | 5/2005 | Evans, III et al. |
| 6,918,893 B2 | 7/2005 | Houde et al. |
| 6,939,302 B2 | 9/2005 | Griffiths et al. |
| 6,972,001 B2 | 12/2005 | Emig et al. |
| 7,094,216 B2 | 8/2006 | Trombley, III et al. |
| 7,389,788 B2 | 6/2008 | Wilson et al. |
| 7,617,837 B2 | 11/2009 | Wilson et al. |
| 7,905,246 B2 * | 3/2011 | Wilson et al. | 137/112 |
| 2002/0128611 A1 | 9/2002 | Kandalaft |
| 2004/0082904 A1 | 4/2004 | Houde et al. |
| 2004/0143212 A1 | 7/2004 | Trombley, III et al. |
| 2004/0221904 A1 | 11/2004 | Usher et al. |
| 2004/0242996 A1 | 12/2004 | Trombley, III et al. |
| 2005/0104444 A1 | 5/2005 | Callan et al. |

FOREIGN PATENT DOCUMENTS

| | | |
|---|---|---|
| JP | H0362113 | 10/1987 |
| WO | 9707841 | 3/1997 |

OTHER PUBLICATIONS

Communication from European associate to the European Patent Office regarding a response to the Official Communication dated Jan. 17, 2011 from the European Patent Office for European Patent Application No. 10 183 298.8, dated Jul. 12, 2011, 15 pgs.

Canadian Office Action for related application CA 2,469,545, mailed on Jan. 21, 2011 (4 pgs.).

Communication from the Canadian Patent Office regarding a Requisition by the Examiner dated Feb. 23, 2012 for Canadian Patent Application No. 2,469,545, 3 pgs.

Translation of Communication from the Brazilian Patent Office regarding an Official Action dated May 15, 2012 for Brazilian Patent No. PI0214778-5, 3pgs.

Response to Canadian Office action for Canadian application No. 2,469,545, filed Aug. 7, 2012, 8 pages.

Communication pursuant to Article 94(3) EPC for European Application No. 10 183 251.7-1265, dated Sep. 20, 2012, 4 pages.

Communication pursuant to Article 94(3) EPC for European Application No. 10 183 298.8-1265, dated Sep. 18, 2012, 4 pages.

Office Action from Brazilian application No. PIO214778-5, officially dated Jul. 26, 2011, translation, 4 pp.

Communication pursuant to Article 94(3) EPC dated Feb. 11, 2009 for counterpart EP application No. 02804796.7 from the European Patent Office (4 pgs.).

Final Rejection in Japanese and English translation from the Japanese Office Action for corresponding Japanese patent No. 2003-551496, dated Dec. 1, 2009 (6 pgs.).

Notice of Reasons for Rejection in Japanese dated Dec. 2008 for counterpart Japanese patent application No. 2003-551496 (4 pgs.).

Notice of Reasons for Rejection translated into English dated Dec. 2008 for counterpart Japanese patent application No. 2003-551496 (4 pgs.).

Supplementary Partial European Search Report for EP 02804796.7-2305 dated Aug. 28, 2006 (2 pgs.).

Extended European Search Report for related application EP No. 10183251.7-1265, mailed on Dec. 14, 2010 (6 pgs.).

Extended European Search Report for related application EP No. 10183298.8-1265, mailed on Dec. 14, 2010 (6 pgs.).

(56) References Cited

OTHER PUBLICATIONS

Japanese Office Action and corresponding Translation for related application JP No. 2003-551496, dispatched on Nov. 16, 2010 (5 pgs.)

Communication from the European Patent Office regarding a Summons to attend oral proceedings pursuant to Rule 115(1) EPC dated Feb. 20, 2012 for European Patent Application No. 02 804 796.7, 4 pgs.

* cited by examiner

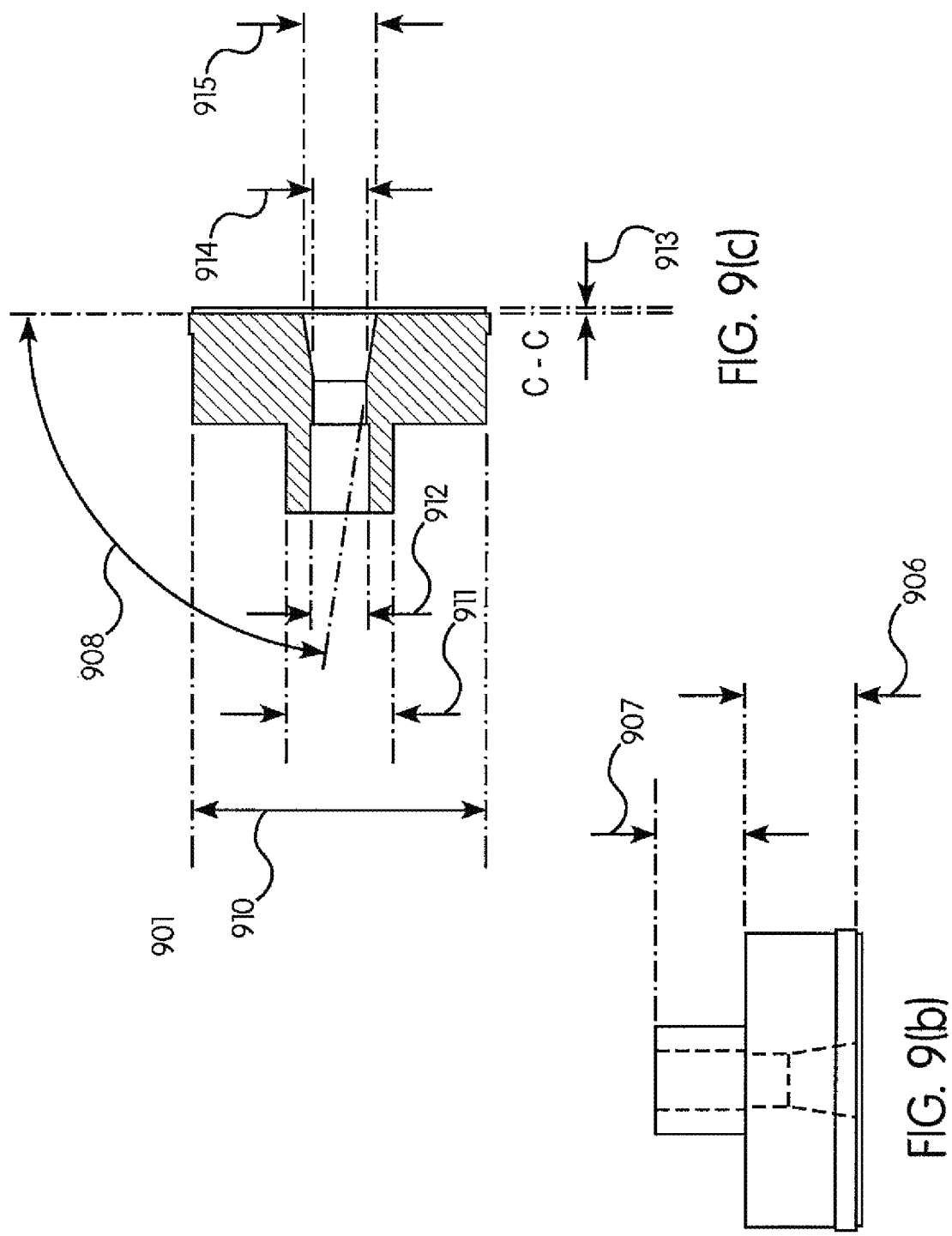

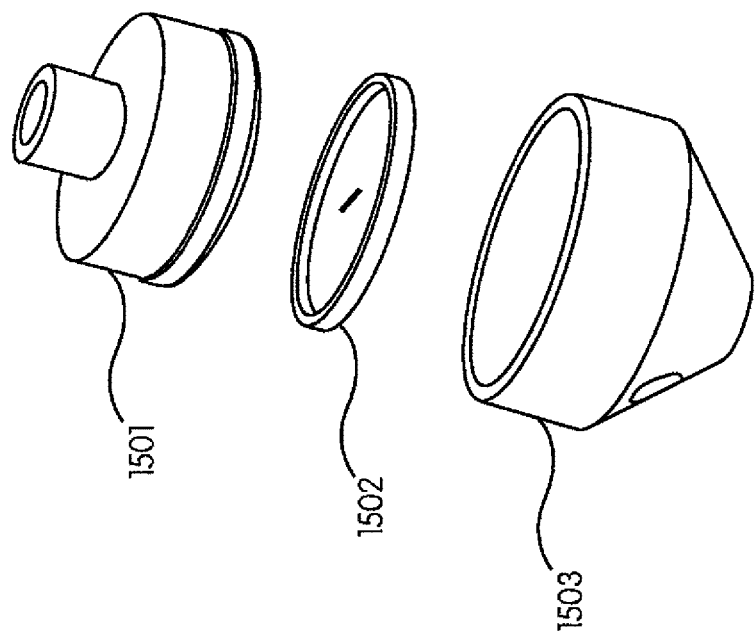
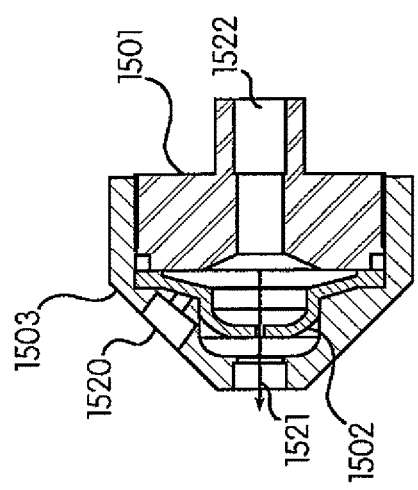
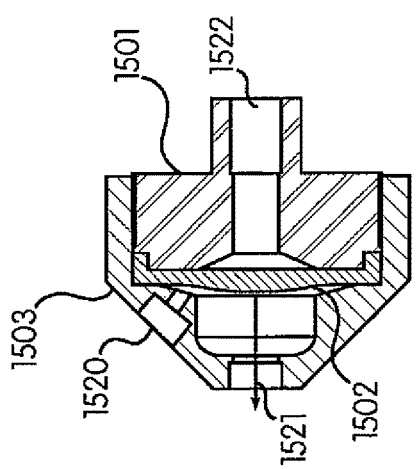
FIG. 15(c)
FIG. 15(a)
FIG. 15(b)

LOW PRESSURE MEASUREMENT DEVICES IN HIGH PRESSURE ENVIRONMENTS

RELATED APPLICATIONS

This application is a continuation of U.S. application Ser. No. 12/575,199, filed on Oct. 7, 2009, now U.S. Pat. No. 7,905,246 which is a continuation application of 11/401,695, filed on Apr. 10, 2006, now U.S. Pat. No. 7,617,837, which is a continuation application of 10/316,147, filed on Dec. 9, 2002, now U.S. Pat. No. 7,389,788, which claims the benefit of U.S. Provisional Patent Application Ser. Nos. 60/338,859 and 60/338,883, each filed on Dec. 7, 2001, all of which are hereby incorporated herein by reference.

FIELD OF THE INVENTION

This invention relates to the field of biomedical technology and, in particular, to methods, systems and apparatus for protecting biological pressure measurement devices in high fluid pressure environments.

BACKGROUND OF THE INVENTION

Certain medical procedures, such as, for example, contrast media injections during cardiological procedures, can require that liquids (such as radiographic contrast agents in, for example, angiography) be injected into a patient's system under high pressures. Such pressures are commonly as high as 1200 lb/in$^2$ (psi) or more than 60,000 mm Hg. While performing such procedures it is also desirable to measure the patient's biological pressures. For example, in angiography it is desirable to record the much lower intravascular and intracardiac pressures—generally falling within the range of −1 to +6 psi—between high pressure injections of the contrast media. Generally, pressure transducers that are designed for physiological measurements cannot tolerate even moderate injection pressures and therefore must be isolated from the fluid path during a high-pressure injection. One such method of isolating pressure transducers is described in U.S. Pat. No. 5,800,397 (Wilson et al.), that uses a manifold to isolate a low pressure system line—where a pressure transducer can be located—from a high pressure contrast medium injection line based on a spool valve concept.

Spool-type manifolds are common in industrial applications and can manage very high pressures. However, such manifolds also require close manufacturing tolerances, are generally expensive, and are designed for use in permanent installations. Also, due to its mechanical "stickiness", the position (open/closed) of a spool-type manifold needs to be monitored by a sensor to avoid malfunction with insipation of blood during a syringe refill. In medical applications, plastic and elastomeric parts are commonly used. This is because pressures are generally low in such environments and sterile parts need to be inexpensive so that for hygienic and safety reasons they can be readily disposed of after a single use. Such polymers have a drawback; they are less conducive to a consistent fit between different parts, which tends to decrease reliability. No device currently exists that combines low cost and ease of manufacture and use with the high pressure capability of industrial valves.

In addition, devices adapted to measure high pressures which would, by definition, be capable of withstanding those pressures, are simply not sensitive enough to accurately measure physiological pressures. Thus, in the example discussed above, a physician performing an angiography using only a high-pressure sensor could, in fact, monitor the injection pressure while contrast material is being injected, but would have no way of monitoring the patient's blood pressure when no injection is occurring. Thus, what is needed in the art is a method of facilitating the deployment of pressure measuring devices—that is sensitive enough to measure physiological pressures—within high fluid pressure environments in a manner that either isolates or protects such devices when high pressures are present.

Thus, within the objects of the present invention are methods, apparatus and systems which facilitate placing devices that make accurate physiological pressure measurements within environments that are intermittently subjected to high pressure fluid flow.

SUMMARY OF THE INVENTION

The present invention presents various novel approaches to solving the problems inherent in measuring biological pressures in high pressure systems. To protect a pressure transducer exposed to fluid flows at higher pressures than its overpressure rating, a novel valve is used that closes a protected leg in which the transducer is located. The various exemplary embodiments of such valves each have a high pressure input, one or more low pressure inputs, and an output. In operation, when a high pressure fluid flow occurs at a high pressure input, the valve automatically closes the low pressure inputs. Alternatively, a novel transducer system is presented, which automatically limits the effective pressure sensed by a transducer to a certain maximum.

BRIEF DESCRIPTION OF THE DRAWINGS

FIGS. 9(*d*) and 9(*e*) illustrate an exemplary valve disc according to the present invention;

FIGS. 15(a)-15(c) depict open, normal, and assembly views, respectively, of an alternate embodiment of the exemplary disc valve of FIGS. 1-9 according to the present invention;

DETAILED DESCRIPTION OF THE INVENTION

Disc Valve Embodiment

It is within the objects of the present invention to provide a valve that is inexpensive, reliable, biocompatible, non-allergenic and able to withstand pressures up to 1500 psi. Moreover, the valve must be able to withstand several modes of sterilization (gamma irradiation, ethylene oxide and e-beam) as well as have a clear housing. It must be easy to remove all bubbles when it is flushed with saline or contrast. The pressure gradients required in the valve are complex. It must have a reliable cracking pressure above 9 psi and, upon opening, ensure that an attached pressure gauge (generally, but not always, located in the saline port, as described below) is never exposed to pressures above approximately 15 psi (1 atm). To achieve this, because generally a pressure sensing connection is very 'stiff', parts of the valve must not project or bulge into the sensing path even at very high pressure conditions. Finally, the components of the valve must not degrade the fidelity of a physiologic pressure signal.

In addition to pressure measurement from a tube system through which a high pressure injection is performed, it is often desirable to infuse fluids, such as physiological saline, into a patient through the same tubing system through which the high pressure injection is made. The valve described herein allows a continuous fluid path to a low pressure infusion reservoir to tubing connected eventually to the patient's blood vessel. Injection from another fluid reservoir will passively close off the low pressure reservoir system, preventing back flow from the high pressure reservoir to the low pressure reservoir.

Figure 1:
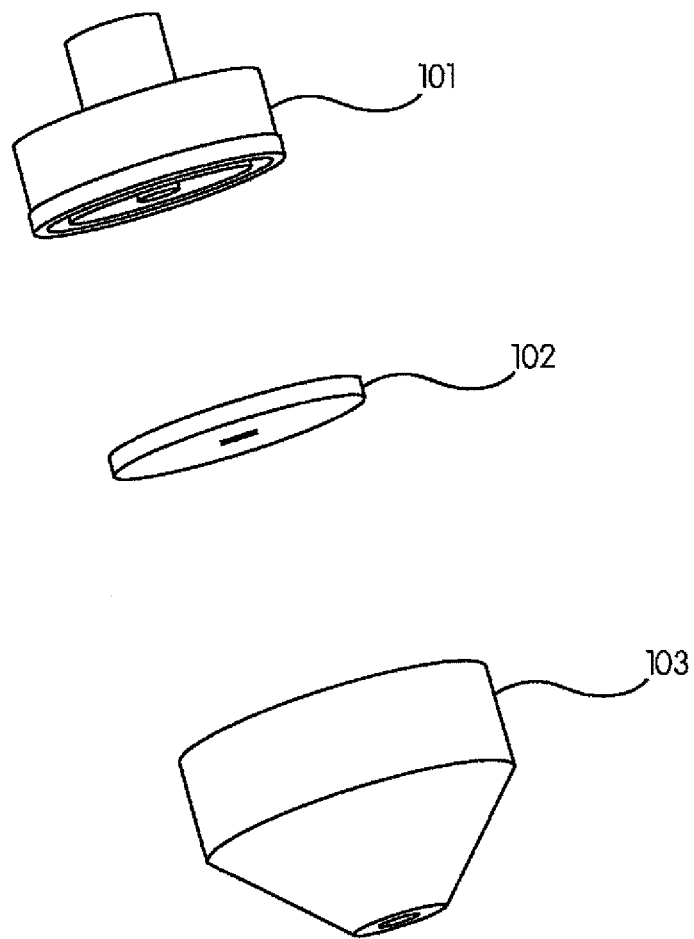
FIG. 1 depicts an expanded view of an exemplary valve assembly according the present invention.

With reference to FIG. 1, an exemplary embodiment of a high-pressure activated valve will be described. An exemplary low and high-pressure elastomeric valve is comprised of a disc holder 101, a middle valve disc 102 and a valve body 103. The valve body 103 and disc holder 102 are made of a relatively rigid polymer, such as for example, polycarbonate, and the valve disc 102 is molded of an elastomer, preferably silicone rubber, with a slit in the center.

The elastomeric disc 102 with the slit is sandwiched between the valve body 103 and disc holder 101 and is affixed at the perimeter of the disc. Such affixation may be effected by, for example, entrapment, adhesion, mechanical or chemical welding, or any other means known in the art. The valve body 103 and disc holder 101 are bonded together, by, for example, sonic welding, UV curable adhesive, mechanical threads or snap (interference) locking, or other bonding or adhesion technologies as may be known in the art, thus entrapping the disc.

In an exemplary embodiment, the valve has at least two, and preferably three, ports that communicate with attached tubing. Such ports are, for example, (a) a contrast inlet port, (b) a saline inlet and pressure transducer port, and (c) a patient or outlet port. In an exemplary embodiment the disc holder 101 contains such a contrast inlet port, as is shown in more detail in FIG. 2, described next.

Figure 2:
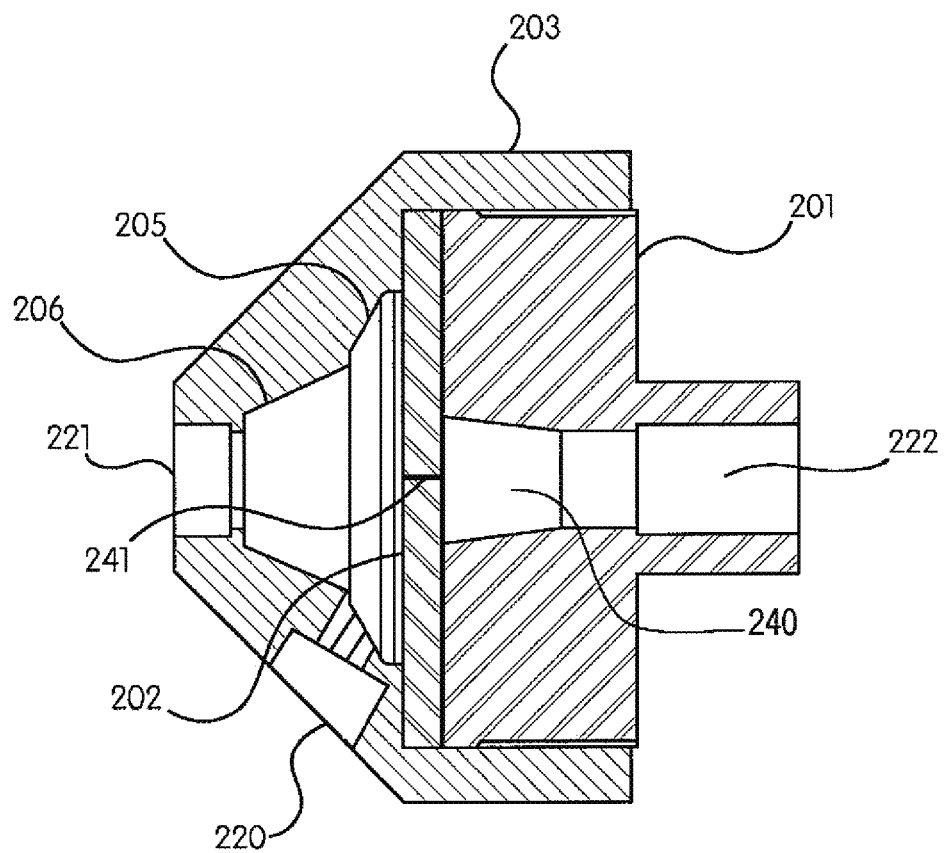
FIG. 2 is a cross sectional view taken along a direction normal to fluid flow of the exemplary valve assembly of FIG. 1 depicting the normal (low pressure) mode of operation.

With reference to FIG. 2, a valve body 203 contains a saline/transducer 220 and a patient/outlet 221 port. Also, a disc holder inlet port hole 222 is tapered outward (in the forward flow direction, i.e., from right to left in FIG. 2) to create a pocket 240 in front of an elastomeric disc 202 so that as fluid travels through the hole 222 and into the empty pocket, air is forced from the pocket (purged) through the disc slit 241 and into the valve body 203 (more precisely, into the cavity in the valve body which is adapted to fluid flow). Thus, for example, in an angiographic procedure as described above, as contrast media fills the empty pocket 240 of the disc holder 201 and pressure thus builds, the elastomeric valve disc 202 bends and eventually opens the slit 241 (which occurs at a certain pressure, known and referred to herein as the 'cracking pressure') to inject fluid into the valve body. The dimensions of the pocket allow for control of the cracking pressure; at a given pressure, exposing a greater surface of the disc to that pressure will increase the force upon a disc and thus lower the cracking pressure. The situation where the slit opens and fluid flows from the inlet port 222 through the slit into the valve body 203 is shown in more detail in FIG. 3, described below.

Continuing with reference to FIG. 2, in an exemplary embodiment a valve body 203 has two internal tapers. A narrow taper 205 closest to the disc 202 that contains the saline port, and a second wider taper 206. In operation, the narrow taper next to the disc 202 allows the saline/transducer port 220 to be sealed as pressure builds up and before fluid passes through the disc 202. The second, wider taper 206 and associated cavity create room for the disc to expand and allow the slit 241 to open fully. The converging angles (in the forward flow direction) also promote flushing of air from the valve so that no bubbles are left behind.

Figure 3:
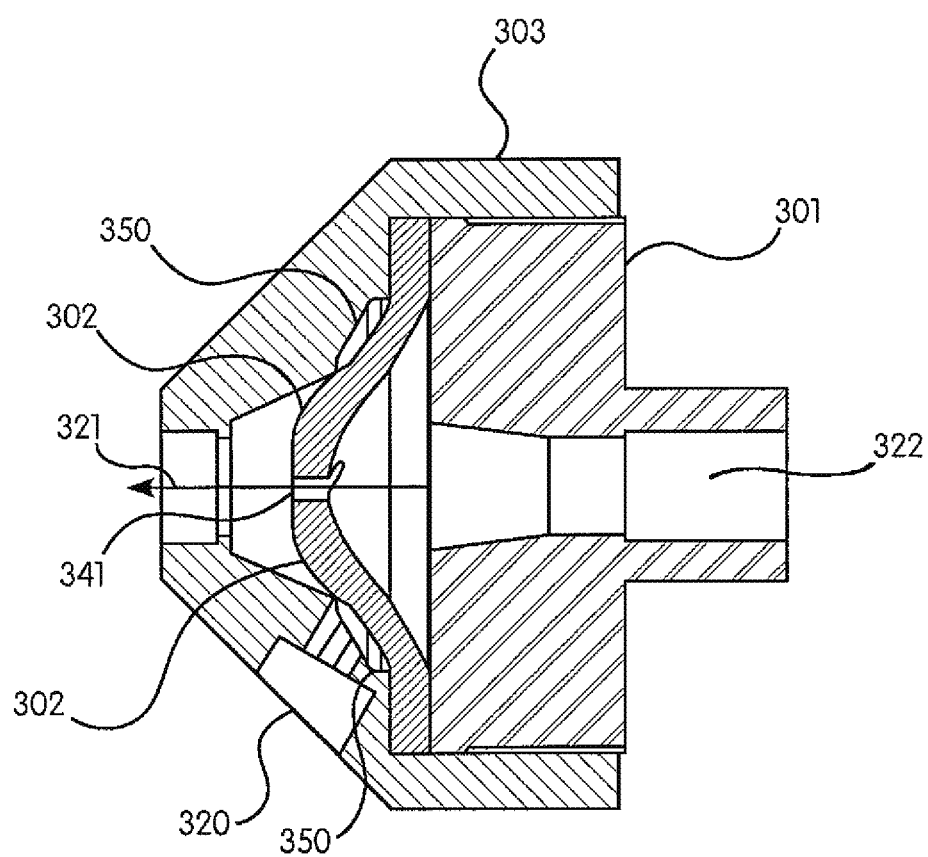
FIG. 3 is a cross sectional view taken along a direction normal to fluid flow of the exemplary valve assembly of FIG. 1 depicting the open (high pressure) mode of operation.

FIG. 3 depicts the exemplary valve of FIG. 2 in the high pressure fluid flow state described above. With reference to FIG. 3 contrast fluid under high pressure flows through inlet port 322. This has caused the pressure applied to the right side of the disc 302 to exceed the 'cracking pressure', which caused disc 302 to expand in the direction of flow (or to the left in FIG. 3), opening the disc slit 341. As the disc expanded it covered the opening of the saline/transducer port 320 in the cavity of the valve body 303. At the same time, the force maintained on the disc 302 by the incoming fluid keeps the saline port shut during high pressure fluid flow, such as, for example, is experienced in a contrast fluid injection. The first taper has, for example, a ring-shaped channel 350 where the saline port 320 is located, thus allowing the interior of the valve body 303 to be completely filled with saline during initial setup. In an exemplary embodiment, the rest of the valve body 303 and the corners of the channel are preferably rounded to eliminate any trapping of air bubbles during setup and. Also, such a channel helps air to be removed by a vacuum applied manually using a syringe.

In exemplary embodiments, the valve can be used in connection with low pressure (60 psi) to high pressure (1200 psi) medical fluid injections. It can also be used with CT, MRI and cardiology contrast media injection systems. Additionally, a two-port version of the valve with the elimination of the saline/transducer port 320 can be manufactured economically enough to act as a check valve. Such a high/low pressure valve is thus inexpensive to manufacture, having a simple design and consisting of three molded parts that can be assembled and bonded together with ease.

The disc holder contains the fluid inlet port and, in exemplary embodiments, can be molded or machined out of, for example, polycarbonate, PET, acrylic or any other tough polymer as may be known in the art that can withstand pressures up to 1500 psi. In exemplary embodiments of the invention the elastomeric disc 202, 302 is preferably circular and may be, for example, molded or cut from sheet silicone rubber or other elastomers including, for example, polyurethane and latex. In preferred exemplary embodiments, properties of an elastomeric disc material are, for example, a durometer in the range of 40-70 A, more specifically, for example, 55 A, a tensile strength of 1000-1500 psi, an elongation of 300-700%, and a tear strength 150-300 lbs./inch. In a preferred exemplary embodiment the disc may be 0.060" thick or may have a range of 0.020" to 0.200" in thickness depending on the durometer, fluid and slit dimensions. In an exemplary embodiment the slit in the middle of the disc is preferably 0.125" long, and may be 0.050"-0.30" in length. In preferred exemplary embodiments the disc has a preferred working surface diameter of 0.580" and may range from 0.250" to 2.00".

The valve body 203, 303 is molded or machined out of, for example, polycarbonate, PET, acrylic or other tough polymers that can withstand high pressures up to 1500 psi. In exemplary embodiments it contains the fluid outlet port 221, 321 and the saline inlet/transducer port 220, 320. In exemplary embodiments the internal shape of the valve body has two tapers 205, 206, the first taper being at an angle from the vertical (i.e., from a plane that is normal to the fluid flow direction, and substantially parallel to the plane the disc surface is in when the disc is non-distended as in FIG. 2) of, for example, 10°-45°, and in a preferred exemplary embodiment 20°, with a width of, for example, 0.020"-0.500", and in a preferred exemplary embodiment 0.115". In exemplary embodiments the saline inlet/transducer port 220, 320 is located in the first taper so that the taper enables the disc 202, 302 to close the saline port 220, 320 when fluid flows from the injection system. In exemplary embodiments the second taper may be at an angle upward from the vertical (as above), for example, 45°-90° and preferably 0.161" deep (depth being measured along the direction of fluid flow) to create space for the disc to expand and the slit 241, 341 to open for passage of fluid through the disc.

In exemplary embodiments the valve is assembled by placing a disc 202, 302 in the valve body 203, 303. Then the disc holder 201, 301 is placed into the valve body 203, 303 and the two parts are, for example, pressed together mechanically or threaded together and either UV-bonded, sonic welded or attached by any equivalent means as may be known in the art. The disc is thus trapped between the valve body and the disc holder all along the disc's outer edge to prevent leaks. In exemplary embodiments the three fluid ports may have, for example, male or female luer threads to conveniently attach to the injection system, patient catheter and saline/transducer system.

Thus, the disc valve of the current invention accommodates both high and low pressure fluid systems. Also more than one port can be provided in the valve body 203, 303, and can thus be closed or opened during injection, e.g. up to 4 saline-type ports and can be used for different purposes, such as drug injection, patient fluid sampling and a separate pressure transducer. For example, during a high or low pressure injection (although high enough to exceed the cracking pressure) all such ports can be simultaneously closed, and when the injection system is OFF all such ports will be open, or "ON" and can be used simultaneously or as required.

Figure 4:
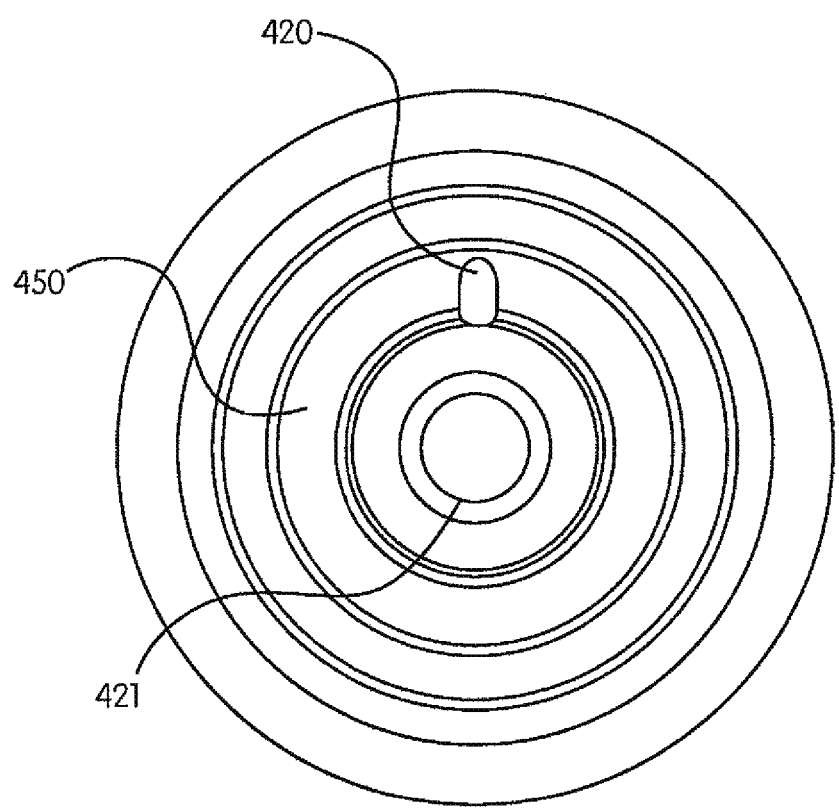
FIG. 4 is a frontal view of the exemplary valve assembly of FIG. 1.

FIG. 4 is a head-on view looking into the contrast fluid output port against the direction of fluid flow. With reference to FIG. 4, besides the contrast fluid output port 421, there can be seen the channel 450, which is an annular ring whose center is the center of the contrast fluid output port and which is positioned relatively close to the edge of the valve disc (unseen in FIG. 4). As was described in connection with FIG. 3, within the channel 450 is the one or more saline/pressure transducer ports 420.

Figure 5:
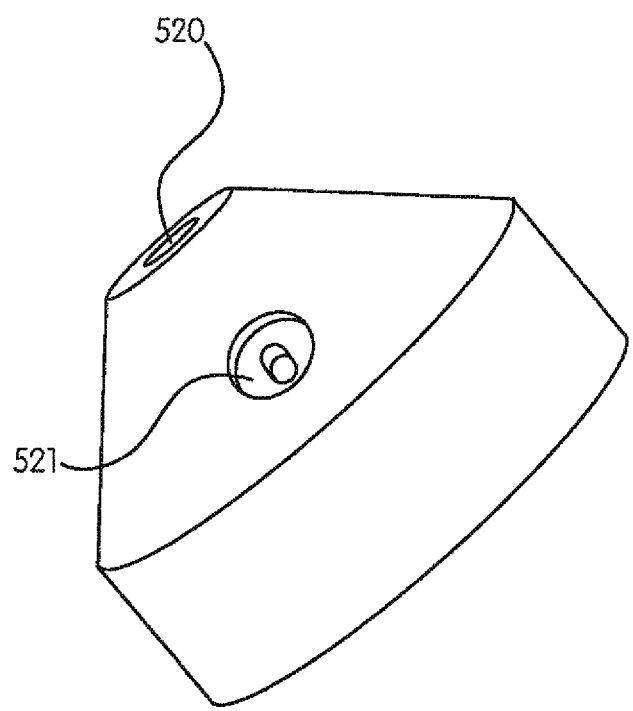
FIG. 5 is a perspective view of an exemplary valve body according to the present invention showing the saline and output ports.

FIG. 5 is a perspective view of the valve body (103 with respect to FIG. 1) showing the contrast fluid output port 521, as well as a saline port 520. It is understood that numerous saline ports could be placed anywhere within the channel (450 with respect to FIG. 4; 350 with respect to FIG. 3) as shall be described below.

Figure 6:
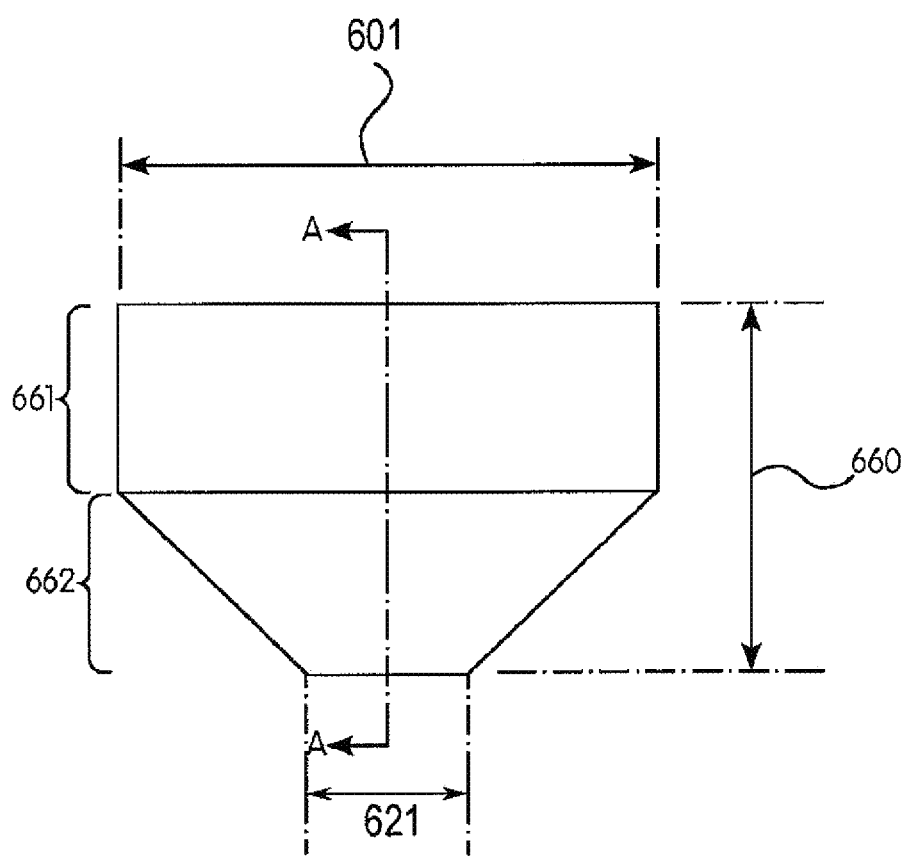
FIG. 6 is a side view of the exemplary valve body of FIG. 5.

FIG. 6 is a side view of the valve body 103 and in the exemplary embodiment depicted in FIG. 6 are shown some representative exemplary dimensions. The overall diameter of the valve body 601 is shown to be one unit, the diameter of the contrast fluid output port 621 is shown to be 0.3 units, overall depth 660 (measured herein along the direction of fluid flow) is shown to be 0.700 units, and the depth of the non-tapered portion of the valve body 661 as 0.35 units. It is understood that the dimensions in FIG. 6 are merely exemplary, and thus show an example of a relationship between the various dimensions of this apparatus. Numerous other dimensions and relationships therebetween are possible and may in fact be desirable, depending on the context and properties of the device that are desired to be accentuated or diminished. For example, the depth of the tapered region 662 is one parameter that controls the cracking pressure. The more room there is in a cavity on the side of the valve disc, the easier it is for the valve disc to be pushed forward (there being less resistance provided by air in a cavity than other possible components), and the lower the cracking pressure. Thus, there is an inverse proportional relationship between the depth 662 and the cracking pressure ("CP"). The greater the area through which a given pressure acts on the disc, the greater the force acting on the disc. Thus CP=k/depth, for some unit determined constant k.

Figure 7:
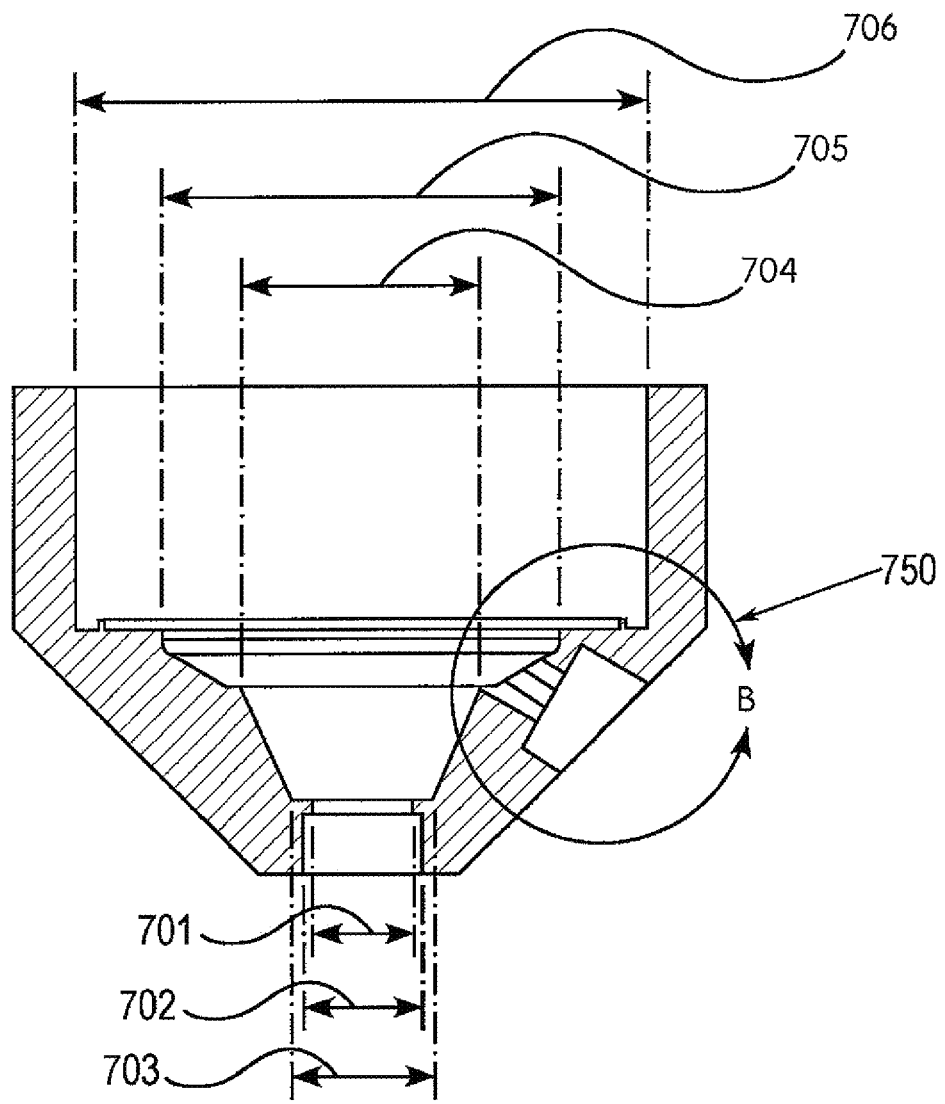
FIG. 7 is a cross section taken at the position A-A of the exemplary valve body of FIG. 6.

FIG. 7 depicts a cross-section along the line A-A of the exemplary valve body depicted in FIG. 6. With reference to FIG. 7, a number of exemplary design dimensions are displayed, such as the inside diameter of the contrast medium output port 701; the outside diameter of that output port 702; the diameter of the cavity at the front edge where the cavity connects into the contrast fluid output port 703; the diameter at the beginning of the second tapered region in the valve body cavity 704; the diameter at the beginning of the first tapered region in the valve body cavity 705; and the inside diameter of the valve body in the non-tapered region 706, which is the diameter into which a given valve disc will fit. As described above, so as not to have any liquid leakage, the diameter of an exemplary disc designed to fit within the diameter 706 will have that same diameter to ensure a tight fit. Exemplary dimensions of 701-706 are, respectively, 0.149, 0.169, 0.210, 0.350, 0.580 and 0.830 units. It is also possible to make the diameter of the disc slightly larger in alternative exemplary embodiments, thus ensuring a tight fit, where liquids of very low viscosity are used which require a greater attention to leakage prevention.

Figure 8:
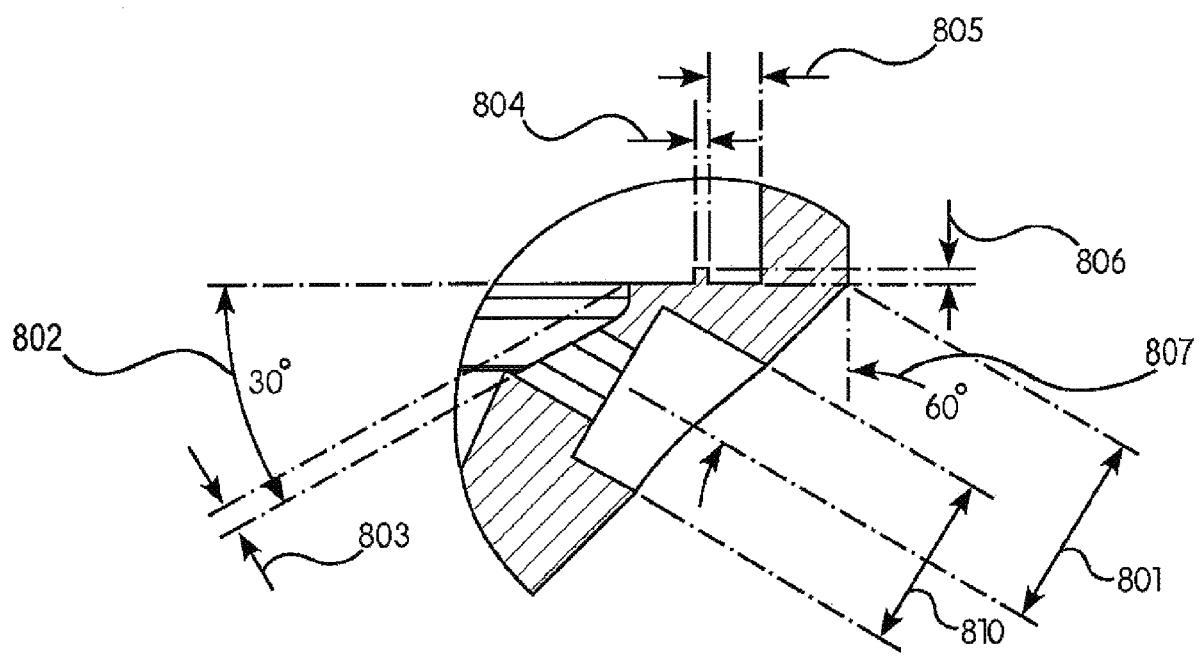
FIG. 8 is a detail drawing of the indicated portion (B) of FIG. 7.
Figure 9A:
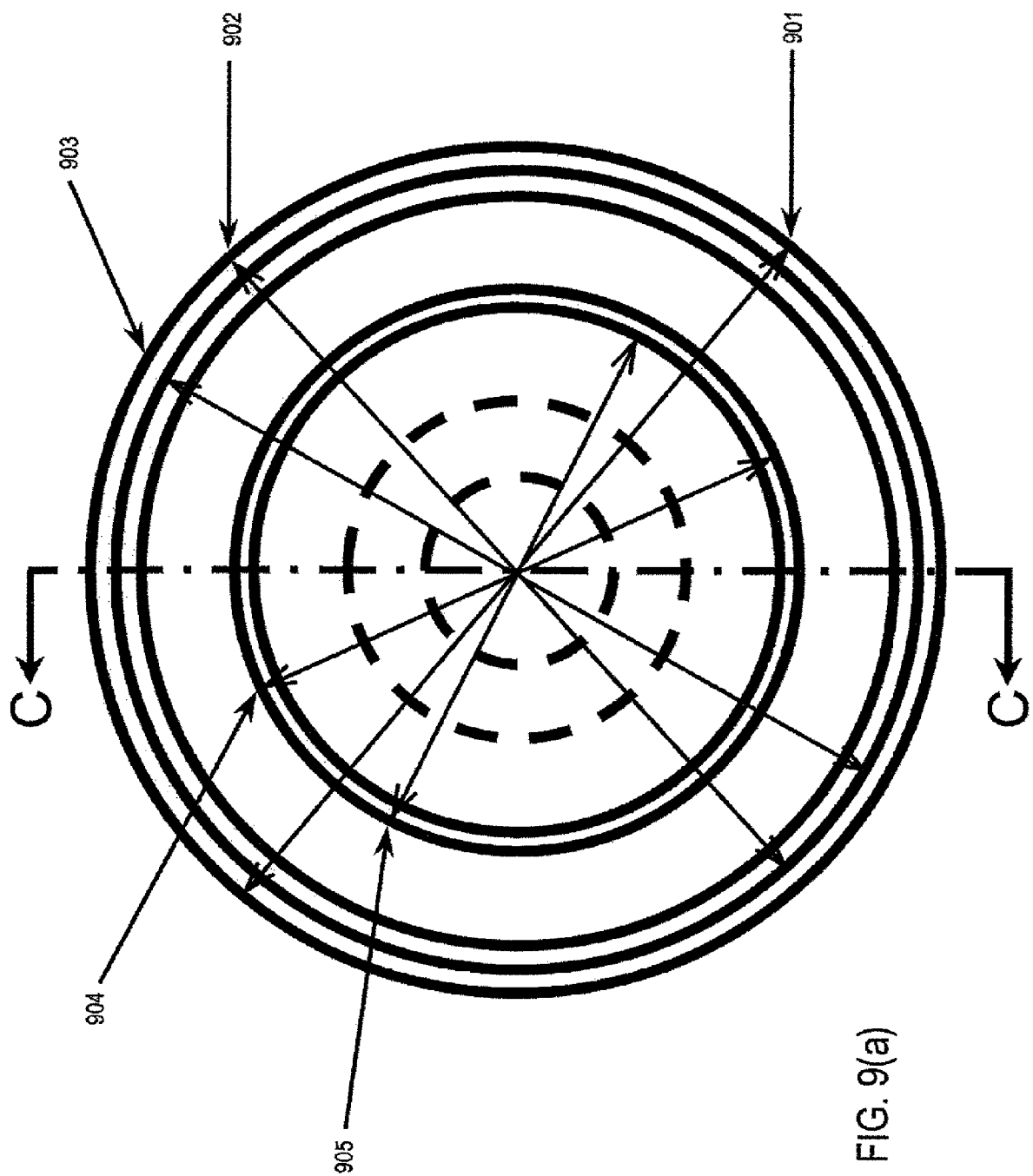
FIGS. 9(*a*)-(*c*) illustrate an exemplary disc holder according to the present invention.
Figures 9D, 9E:
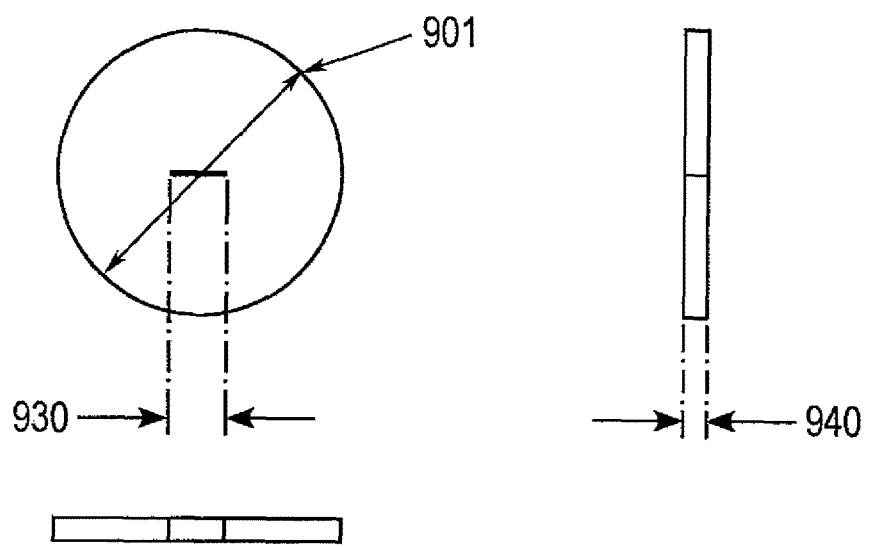

It is noted that for the exemplary embodiment depicted in FIG. 7, an exemplary valve disc designed to fit therein is depicted in FIG. 9(*d*) in horizontal top view and in FIG. 9(*e*) in a vertical side view showing. With reference to FIG. 9(*d*) it can be seen that the diameter of the depicted exemplary valve disc is 0.83 units, identical to the dimension depicted in FIG. 7 element 706. As can be seen with reference to FIG. 7, there is a region 750 depicted as being surrounded by a circle labeled "B." This region is depicted in FIG. 8, as shall next be described.

FIG. 8 depicts the detailed B region in a scale magnified by a factor of 6 relative to FIG. 7. The area of detail depicted in FIG. 8 is, as should be obvious to the reader, the exemplary saline port within the valve body. With reference to FIG. 8, it can be seen that angle 807, representing the angle of the outer taper of the valve body is, in this exemplary embodiment, 60° off of the vertical and that the distance from the corner where the outer tapered region begins in the outer surface of the valve body to the center of the saline port is, in this exemplary embodiment, 0.192 units 801. Also, angle 802, which represents the angle of the inner taper or the first taper 205 (with reference to FIG. 2) is shown to be 30° in this exemplary embodiment. The exemplary diameter of the saline port 810 is 0.169 units. As well, with reference to FIG. 8, 803 indicates channel depth to manually purge air from the transducer side of the system (which does not require if it is auto purged), 804 a width of an indent to clamp a valve disc positively, 805 a location of an indent to clamp a valve disc positively, and 806 a height of an indent for clamping a disc. In this exemplary embodiment, 803-806 are, respectively, 0.025, 0.013, 0.050, and 0.015 units.

With reference to FIGS. 9(*a*) through 9(*c*), there are depicted various views of the disc holder 101 (with reference to FIG. 1) in the following exemplary dimensionalities. With reference to FIG. 9(*a*), an exemplary outward diameter 901 is 0.83 units. It is noted that this dimension corresponds to element 706 in FIG. 7, which is precisely the exemplary dimension into which the inner diameter of the non-tapered portion of the valve body into which the disc holder is to fit. As well, index numbers 902-905 represent exemplary inner diameters of the depicted exemplary disc holder, which are 0.810, 0.785, 0.652 and 0.600 units, respectively. With reference to FIG. 9(*b*), 906 shows an exemplary height of a main portion of an exemplary disc holder, 0.300 units, and 907 an exemplary height of the high pressure input port, 0.250 units. With reference to FIG. 9(*c*), 910 shows an exemplary diameter of a main portion of an exemplary disc holder, 911 an exemplary outer diameter of the high pressure input port, 912 an exemplary inner diameter thereof, 914 an exemplary port size for creating sufficient pressure, 915 an exemplary pocket size for creating pressure, and 908 an exemplary pocket angle of 82° (from the vertical) for an exemplary pocket, and 913 an exemplary height of a protrusion for clamping within the indent shown in FIG. 8. In this exemplary embodiment, 910-915 are, respectively, 0.810, 0.300, 0.169, 0.015, 0.149 and 0.200 units.

With reference to FIGS. 9(*d*) and 9(*e*), views of and exemplary dimensions for an exemplary valve disc are shown. With reference to FIG. 9(*d*), as discussed above, an exemplary outer diameter of the valve disc is shown as 0.83 units. The exemplary disc slit length 930 is shown as 0.15 units. It is noted that given the relationship between the disc length and the diameter of the valve disc, even when the valve disc slit is completely open, there is no concern for leakage at the perimeter of the valve disc. Thus, one or more additional saline ports could be placed anywhere within the annular ring identified as the channel 350 with respect to FIG. 3, which would identically and simultaneously be closed upon the currents of the configuration of the valve depicted in FIG. 3. With respect to FIG. 9(*e*), 940 the thickness of the valve disc is shown and an exemplary thickness of the valve disc shown here in this exemplary embodiment having 0.06 units of thickness.

The design parameters are used to set a cracking pressure for the valve. In general cracking pressure is a function of disc thickness, slit length, durometer of the elastomeric disc and the primary taper of the valve body. Cracking pressure increases with increasing disc thickness and disc material durometer, and cracking pressure decreases with decreasing slit length of the disc and primary taper of the valve body.

Rotary Valve Manifold Embodiment

Figure 10:
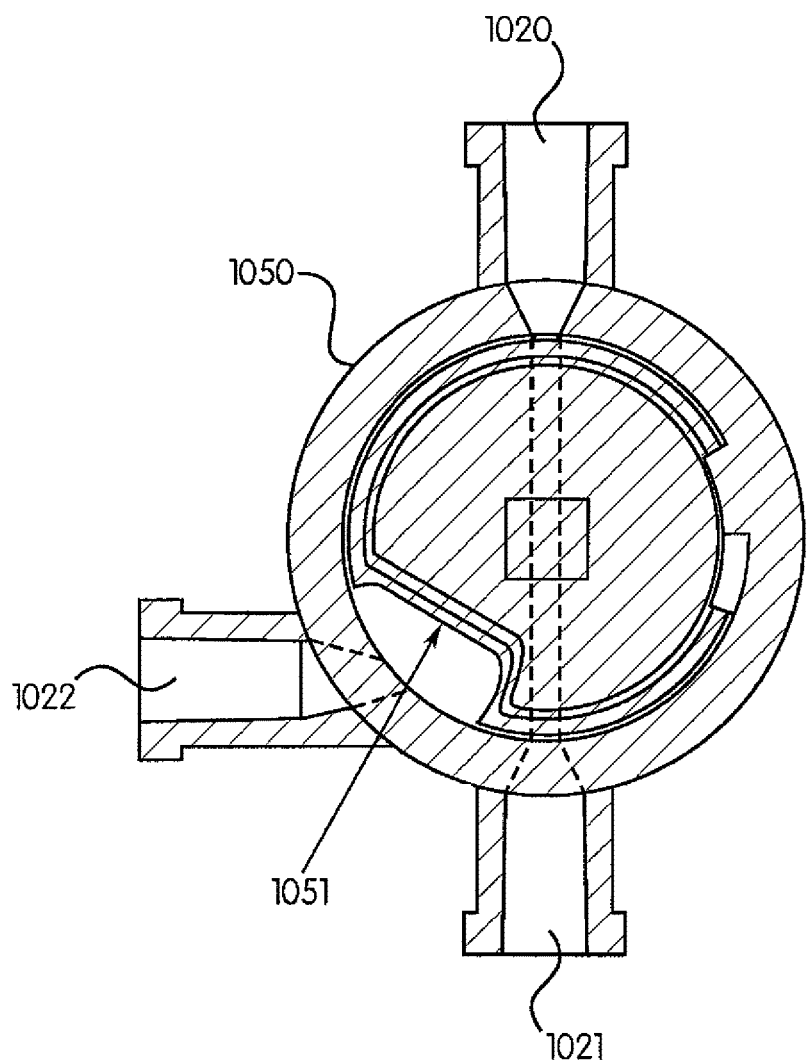
FIG. 10 depicts an exemplary rotary valve manifold according to the present invention in the normal mode.

In an alternative exemplary embodiment, a rotary valve apparatus is utilized to switch between the high pressure and low pressure environments. FIG. 10 depicts an exemplary rotary valve embodiment according to the present invention. With reference to FIG. 10, an exemplary rotary valve is a three-piece design, comprising an outer housing 1050 and an inner rotating seal 1051. In preferred exemplary embodiments the three pieces should be molded using, for example, polycarbonate, or as a specific example, Makrolon Rx-2530. In an exemplary embodiment the internal rotating seal is preferably molded using TPE. FIG. 10 shows the valve in a static state. There is a path from the saline port 1020 through the center of the TPE seal 1051 to the patient output port 1021, but there is no open fluid path to the patient output port 1021 from the contrast media port 1022.

Figure 11:
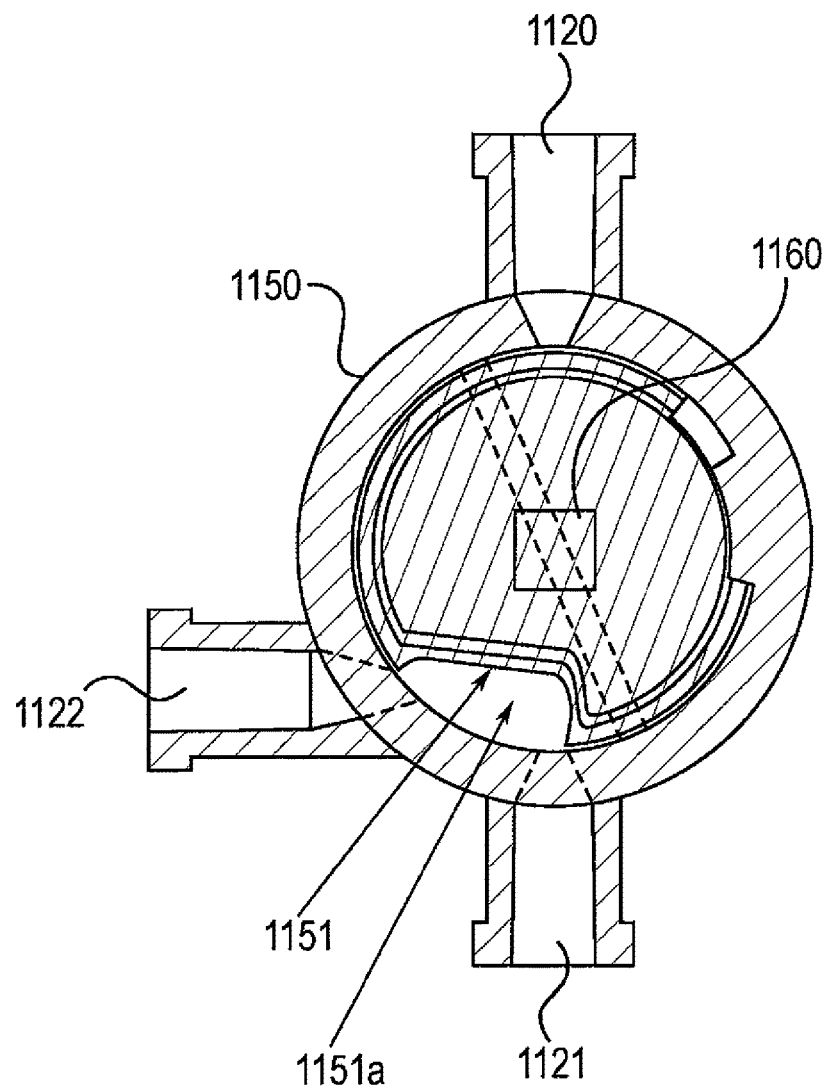
FIG. 11 depicts the exemplary rotary valve manifold of FIG. 10 in the open mode.

FIG. 11 depicts the situation where the valve is open for contrast media. When contrast media is injected at port 1122, fluid dynamics puts more pressure on the front of the seal cavity 1151(*a*), thus rotating the disc counterclockwise approximately 25 degrees (this angular measure being a function of the angular arc that the inner seal must travel before a fluid path between contrast and patient is established, itself a function of the device geometries) before pressure equalizes in the chamber as a result of an open path for the contrast media through the patient output port 1121. Thus, this rotation of the inner seal closes the saline fluid path and opens a contrast media to patient fluid path. In addition, the rotation of the inner seal stores energy in the twist or torsion in the member 1160 which protrudes from the inner seal to hold the inner seal 1151 in the housing 1150. Such member is, in the depicted exemplary embodiment, a 3D rectangular structure whose cross section is a square whose centroid is the axis of rotation of the inner seal 1151, but such member can be any of a variety of shapes as may be known in the art. When pressure drops at the contrast media connection, the seal rotates back to the static state, closing the contrast media port 1122 and opening the saline path 1120.

Figure 12A:
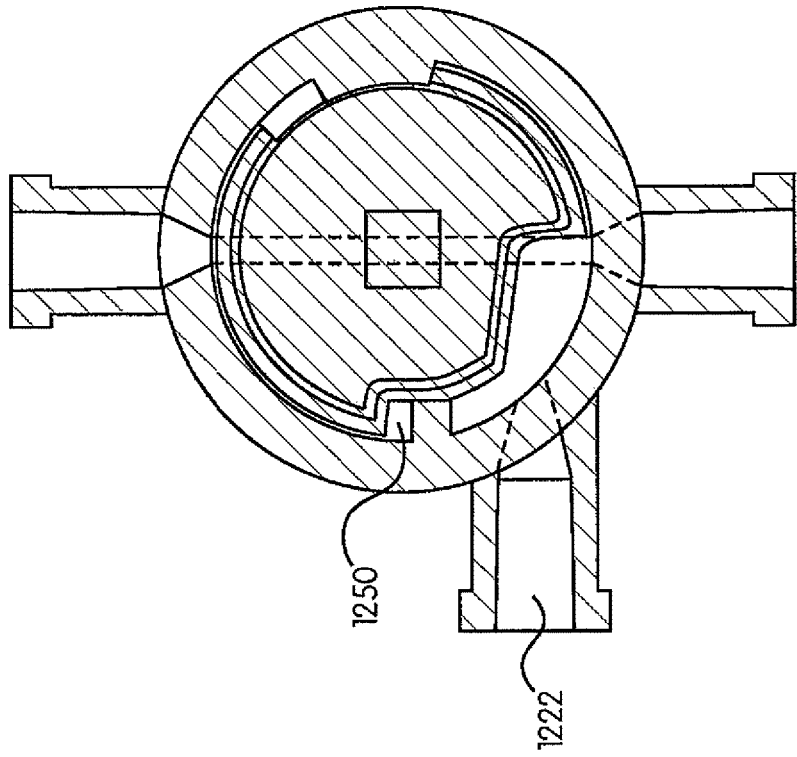
FIGS. 12(*a*) and 12(*b*) depict an alternative exemplary rotary valve manifold according to the present invention in the normal and open modes, respectively.
Figure 12B:
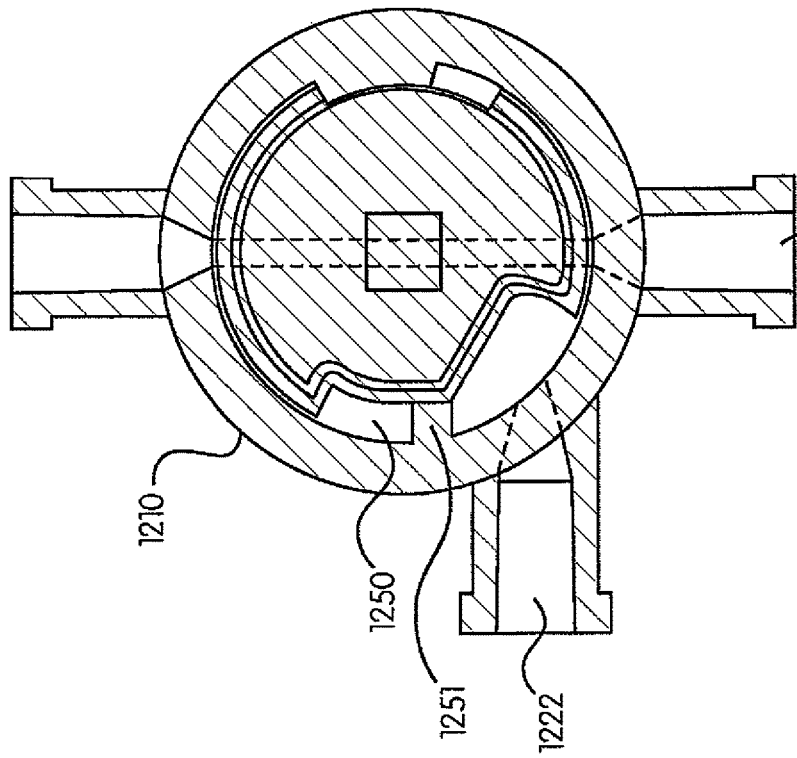

FIGS. 12(*a*) and 12(*b*) respectively depict an alternative exemplary embodiment of the rotary valve of FIGS. 10-11. As indicated in FIG. 12(*a*), this exemplary embodiment utilizes an additional protrusion 1251 of the valve housing 1210 into the central rotary seal area creating an air gap 1250 that is compressed when the valve goes into the open state as depicted in FIG. 12(*b*), thus storing potential energy in the compression of the air in the air gap 1250. This air gap assists the rotary seal to return to the normal state of FIG. 12(a) when there is no longer any high pressure flow entering the contrast input port 1222 and exiting the outlet port 1221, as the compressed air exerts a net torque (directed into the plane of the drawing) on the rotary seal which is no longer balanced by any torque resulting from the high pressure flow. In alternative exemplary embodiments, the air gap could be replaced by a more compressible material relative to the rotary seal, or the air gap could be contained within the rotary seal without being exposed to the housing.

Plunger Valve Embodiment

Figure 13:
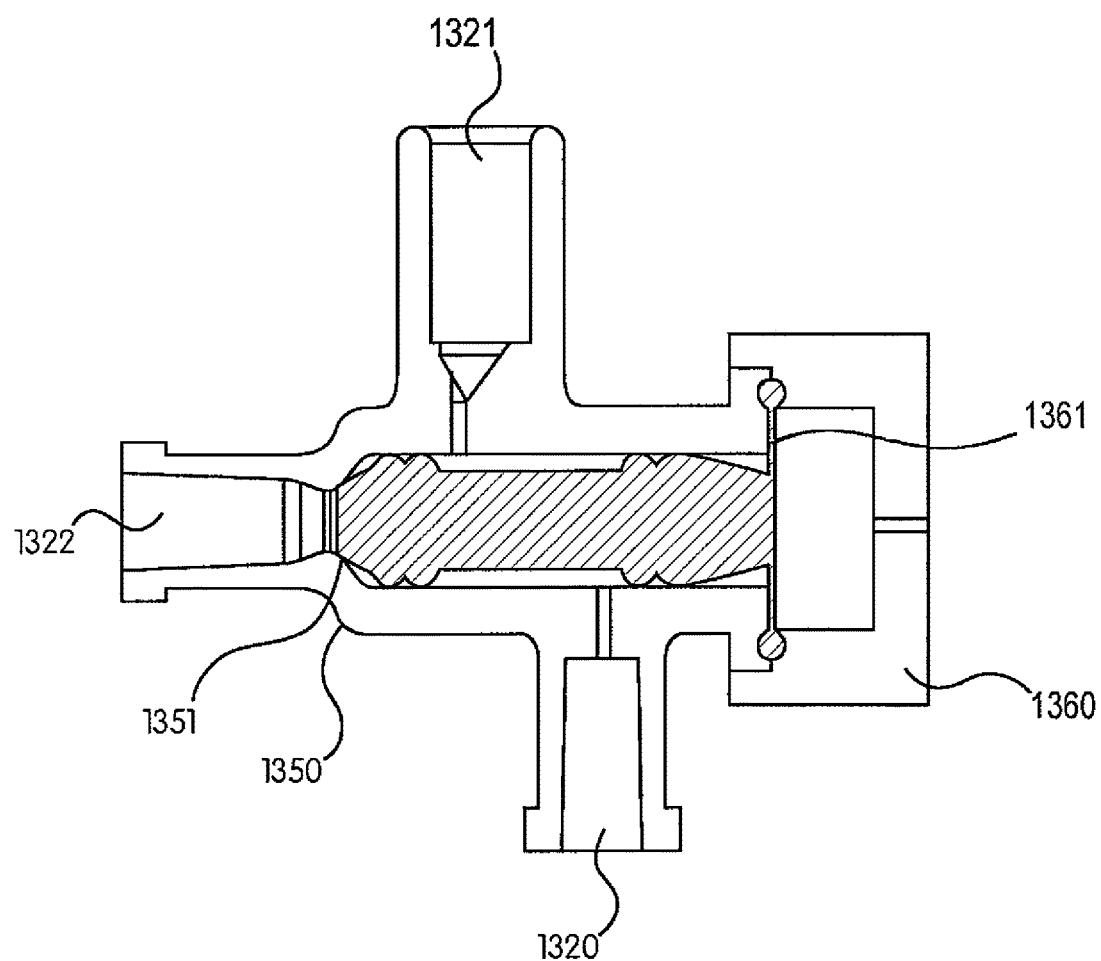
FIG. 13 depicts an exemplary plunger manifold valve according to the present invention in the normal mode.
Figure 14:
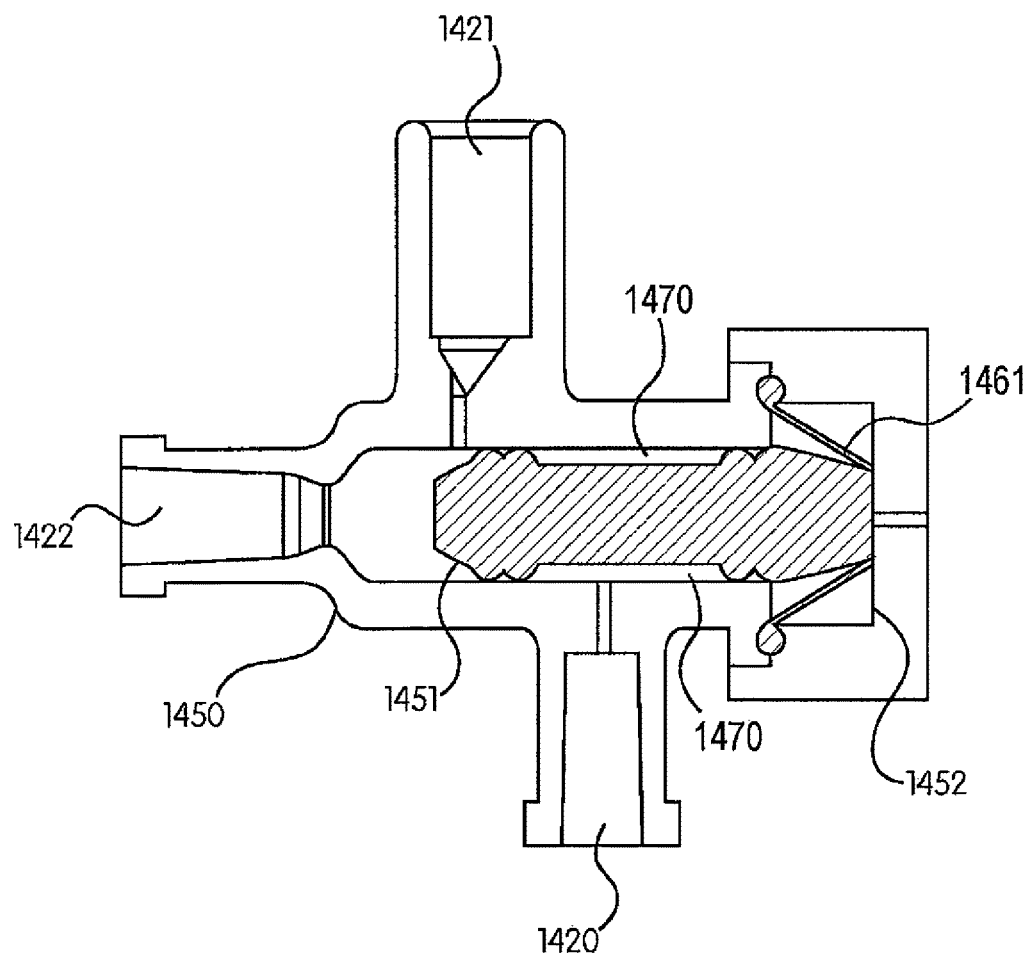
FIG. 14 depicts the exemplary plunger manifold valve of FIG. 12 in the open mode.
Figure 16C:
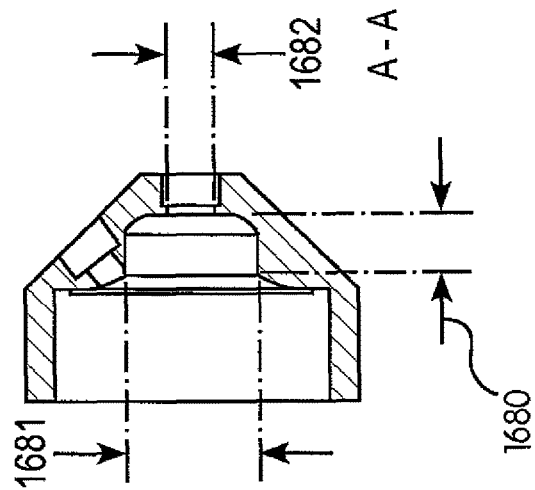
FIGS. 16(a)-16(d) depict exemplary relative dimensionalities of a valve body for the exemplary disc valve of FIG. 15.
Figure 16A:
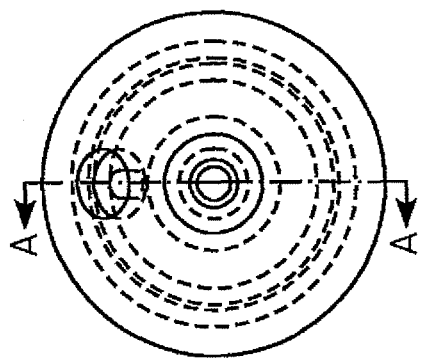
Figure 16B:
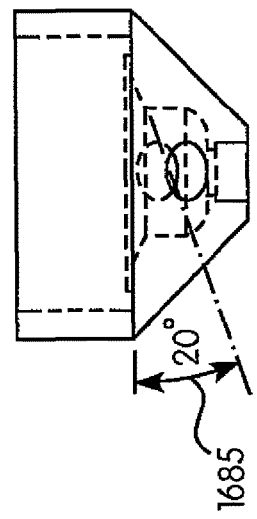
Figure 16D:
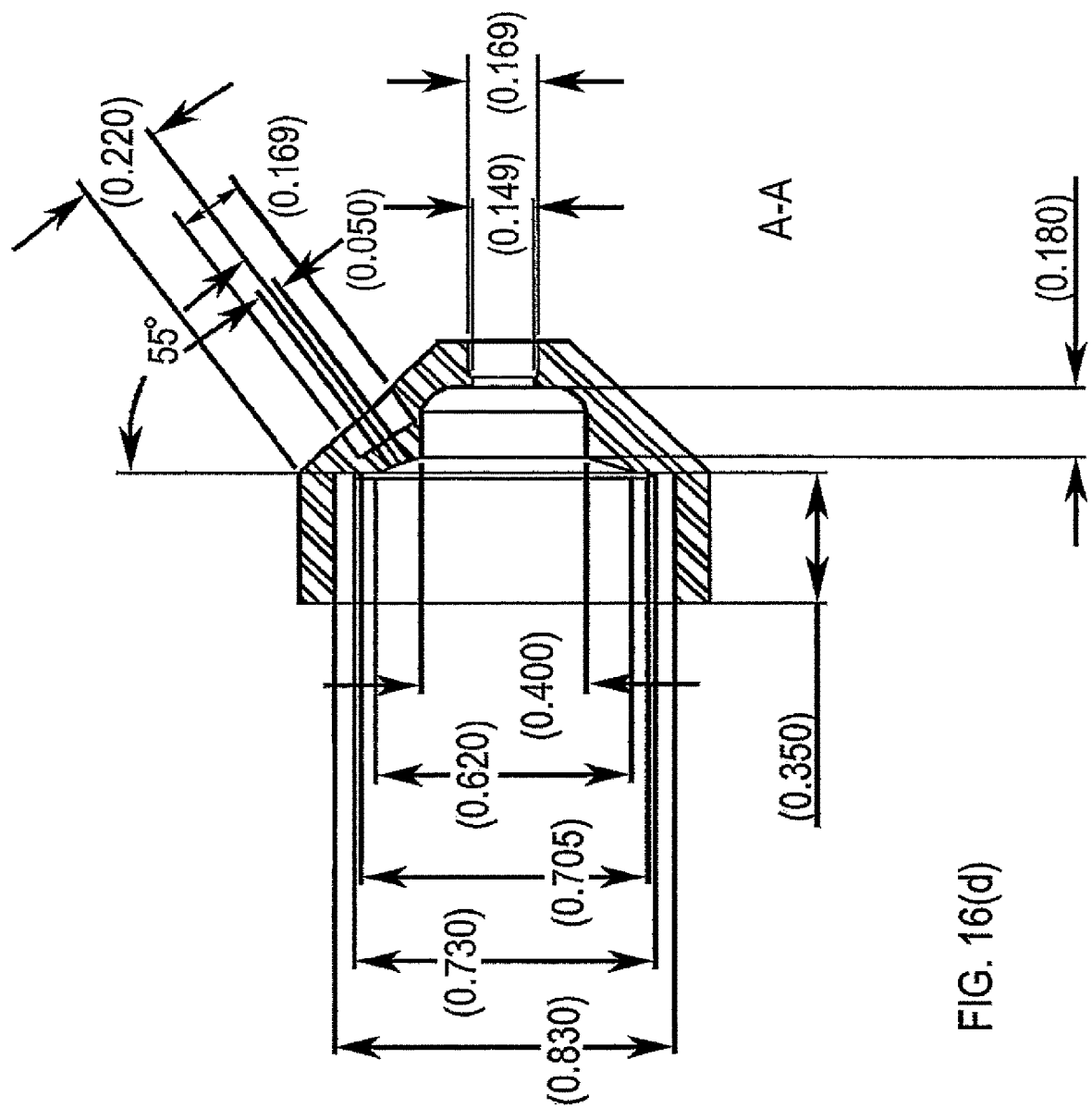

With reference to FIGS. 13 and 14, an alternative exemplary embodiment of the invention is next discussed. These Figures depict the normal and open states, respectively, of an exemplary plunger valve. This design uses a minimum of parts (three in the depicted exemplary embodiment). With reference to FIG. 13, the normal state is depicted, including the saline inlet port 1320, contrast inlet port, 1322, and outlet port 1321. The manifold body 1350, 1450 and end cap 1360 can be molded using, for example, a polycarbonate such as, for example, Makrolon Rx-2530. The internal plunger 1351 with diaphragm 1361, 1461 may be molded using, for example, a 70 durometer EPDM, polyisoprene or equivalent material as may be known in the art.

FIG. 14 shows the valve in a normal or static state. The path for saline 1420 is open and saline flows around the internal plunger 1451 by means of indentations 1470 caused by a reduced diameter of the plunger 1451 at its central portion. FIG. 14 shows the valve open for contrast media. When the valve sees pressure on the contrast connection 1422 the internal plunger 1451 is pushed back (rightward in the diagram) towards the end cap inside face 1452 and the diaphragm 1461 stretches back (creating potential energy). This closes the saline fluid path 1420 and opens the contrast media to patient fluid path. When pressure drops at the contrast media connection 1422 the stretched diaphragm 1461 pushes the plunger 1451 back to the normal state, as depicted in FIG. 13. This closes the contrast media port 1422 and opens the saline path 1420, 1421.

Alternate Disc Valve Embodiment

In connection with FIGS. 15a through 15c, an alternative embodiment of the disc valve will be next described. FIGS. 15(a), 15(b) and 15(c) are alternative exemplary embodiments of the disc valve, and correspond respectively to FIGS. 3, 2 and 1, showing a variant of the exemplary disc valve depicted in those Figs. Hence, merely the differences between the exemplary embodiment of FIGS. 1-3 and the exemplary embodiment of FIGS. 15(a) through 15(c) will be noted. With reference to FIG. 15(a), there is a contrast fluid input port 1522, an output port 1521, and a saline input port 1520. As can be seen with reference to FIG. 15(a), there are the same components in this exemplary embodiment as there were in the exemplary embodiment presented above, i.e., a disc holder, a valve body, and a valve disc. What is notable about the exemplary embodiment of FIGS. 15(a) through 15(c) is the shape of the cavity within the valve body 1503, as well as the differences in the shape of the taper where the contrast fluid input port 1522 contacts the valve disc 1502. A comparison of FIGS. 2 and 3 with FIGS. 15(b) and 15(a), respectively, shows that the cavity within the valve body 1503 in the exemplary embodiment depicted in FIG. 15(a) is significantly larger than that of FIG. 3. Further, it has more the shape of a rectangle with rounded corners, rather than a trapezoid, such as is created by the first and second tapers, with reference to FIGS. 2 and 3. This results in a lower cracking pressure, inasmuch as there is less resistance to the forward movement of the valve disc 1502 than there is in the exemplary embodiment depicted in FIGS. 3 and 2, respectively. Also, one can see that the saline input port 1520 in FIG. 15 is placed on the top, as opposed to having them placed on the bottom as in FIGS. 2 and 3. As described above, one or many saline ports can be provided within the channel and their placement is arbitrary and will, in general, be a function of the design context.

With reference to FIG. 15(c) and by comparison with FIG. 1, it can be seen that there is some change in the exemplary embodiment depicted in FIG. 15(c) relative to that of FIG. 1 as concerns the valve disc 1502, 102. In FIG. 15(c) the valve disc 1502 is not purely flat but has a lip on the rearward or topward in the diagram side. FIGS. 16(a) through 16(d), 17(a) through 17(b) and 18(a) through 18(d) provide exemplary relative dimensions of various components of the disc valve of FIGS. 15a through 15c. FIG. 16 collectively provide exemplary relative dimensions for the internal profile of the exemplary valve body. Exemplary dimensions in such exemplary valve body design which are useful in controlling performance are, for example, inner cavity length 0.180 1680, inner cavity height 0.400 1681, output port diameter 0.149 1682 and 20° taper 1685. Such parameters are used to achieve desirable shutting of the saline/transducer port and maintain balanced fluid dynamics.

Figure 17A:
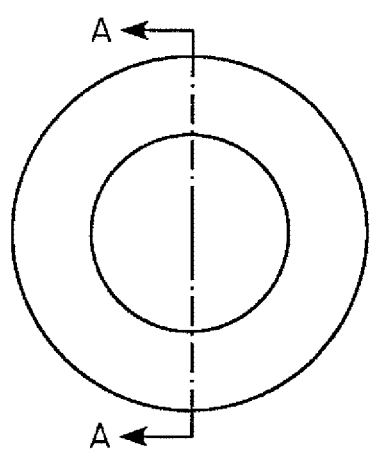
FIGS. 17(a)-17(b) depict exemplary relative dimensionalities of a valve disc for the exemplary disc valve of FIG. 15.
Figure 17B:
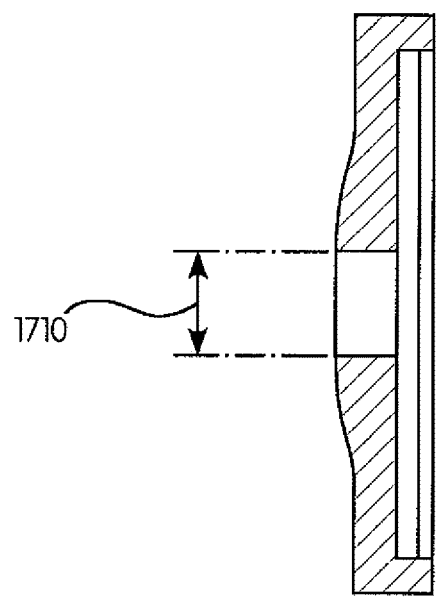
Figure 18A:
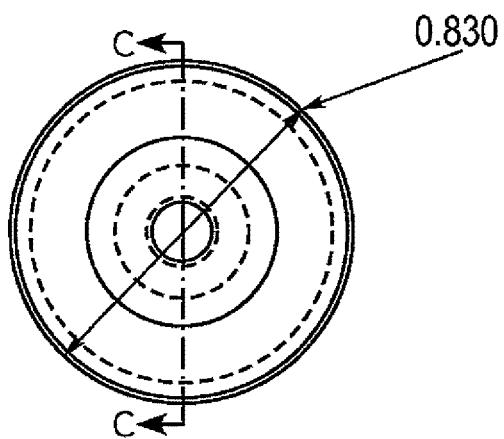
FIGS. 18(a)-18(d) depict exemplary relative dimensionalities of a disc holder for the exemplary disc valve of FIG. 15.
Figure 18C:
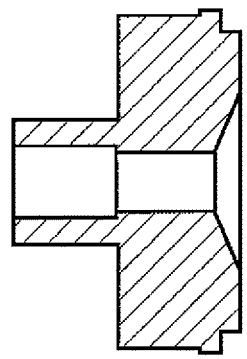
Figure 18B:
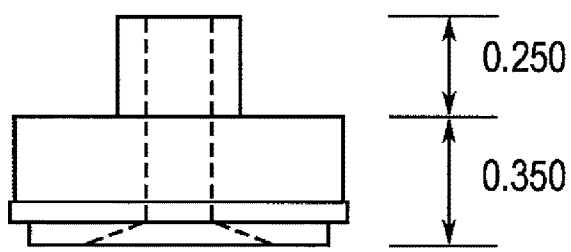
Figure 18D:
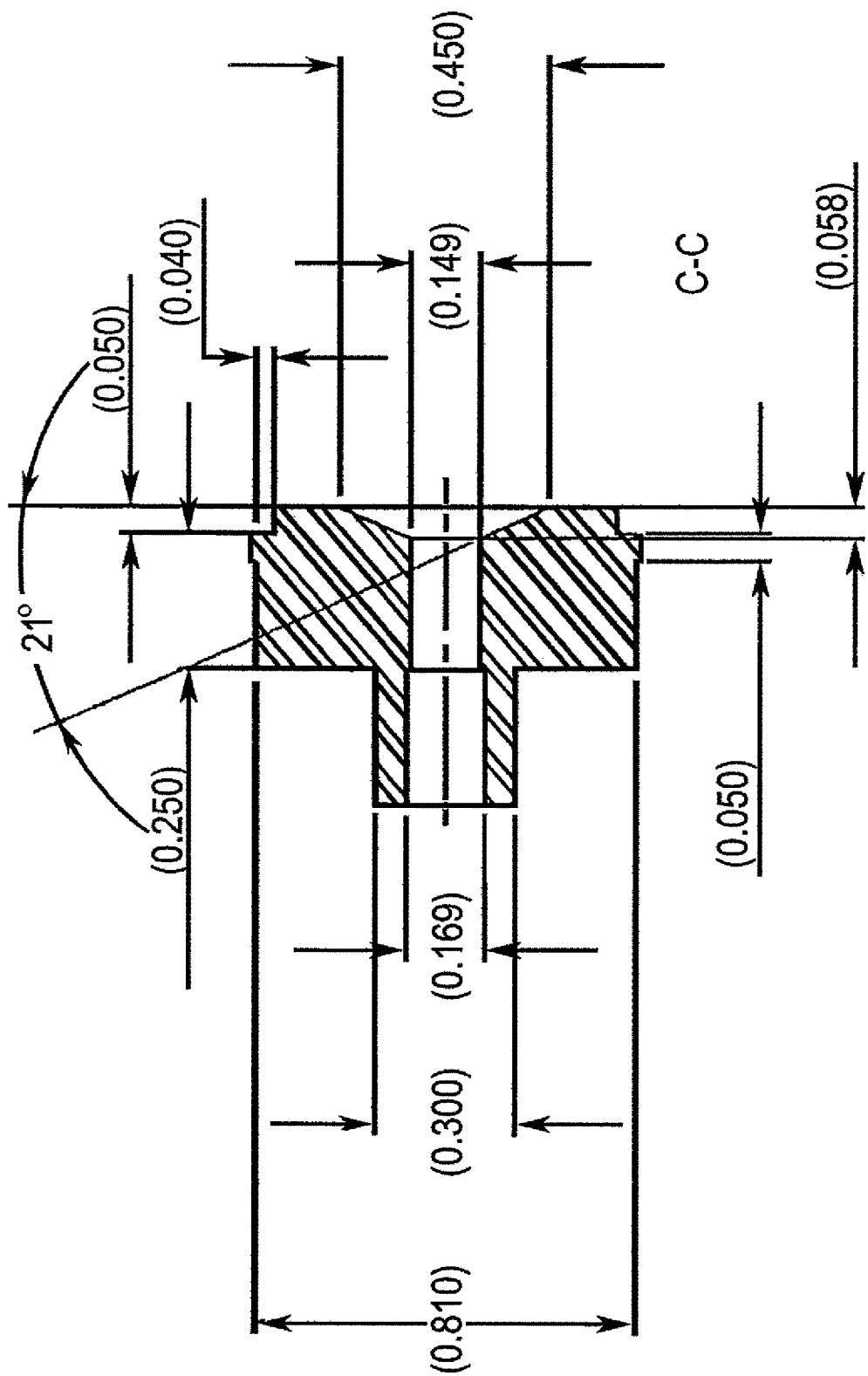

FIG. 17 collectively provide exemplary dimensionalities for the valve disc according to this alternative exemplary embodiment. It is noted that FIG. 17(b) depicts a cross-section along the line A-A in FIG. 17(a) across a diameter of the entire disc, and in the depicted orientation the slit runs vertically and is depicted as 1710 in FIG. 17(b). Further, with reference to FIG. 17(b), one can see the lip structure of this exemplary embodiment of the valve disc as discussed above.

The exemplary disc design of FIG. 17(b) having a bulge on one side in the middle helps in bending the disc to close a saline/transducer port quickly. Also, this exemplary feature increases cracking pressure and prevents the disc from inverting due to any increase in back pressure. In alternative exemplary embodiments the slit in the disc 1710 may have a taper, i.e., be at an angle with the horizontal, which can increase cracking pressure by 25% and also help prevent inversion of the disc due to any increased back pressure.

Accordingly, the disc holder, as shown in FIG. 18, includes a 21° taper from the exemplary dimensions of 0.450 to 0.149 to accommodate the bulge in the disc in order to increase the cracking pressure and prevent inversion of the disc.

Finally, FIGS. 18(a) through 18(d) give exemplary relative dimensions of the disc holder 1501 in FIG. 15(c). As above, these relative dimensions are merely exemplary and numerous other dimensions could be utilized changing some or all of the dimension relationships depicted in FIGS. 16 through 18 collectively, as may be implemented by one skilled in the art.

Figure 19:
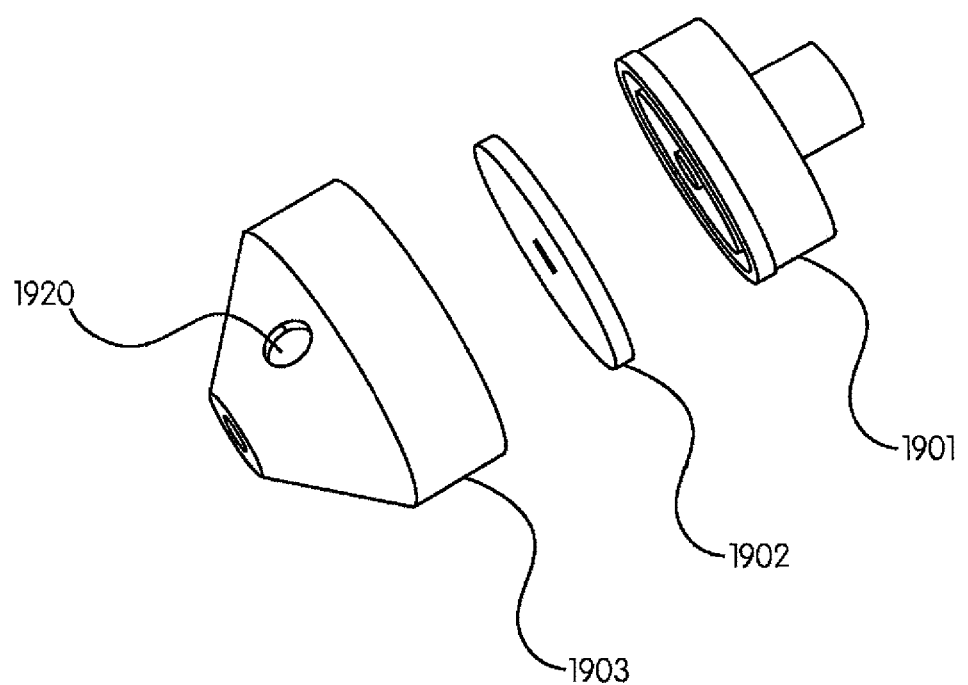
FIG. 19 depicts an exemplary 3D rendering of the exemplary disc valve of FIG. 15.

FIG. 19 is a 3D rendering of the components of the disc valve of FIGS. 15 through 18 showing the three components, the valve body 1903, showing the saline port 1920 provided within it, the valve disc 1902 and the disc holder 1901.

Spool Valve Embodiment

Figure 20:
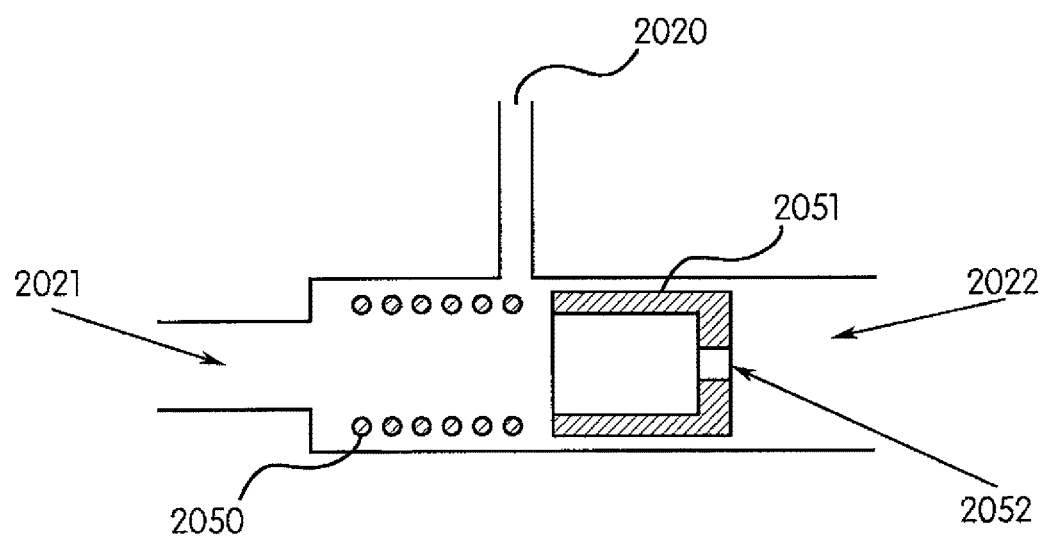
FIGS. 20(a) and 20(b) depict the normal and open views, respectively of an exemplary sleeve shuttle valve according to the present invention.
Figure 20B:
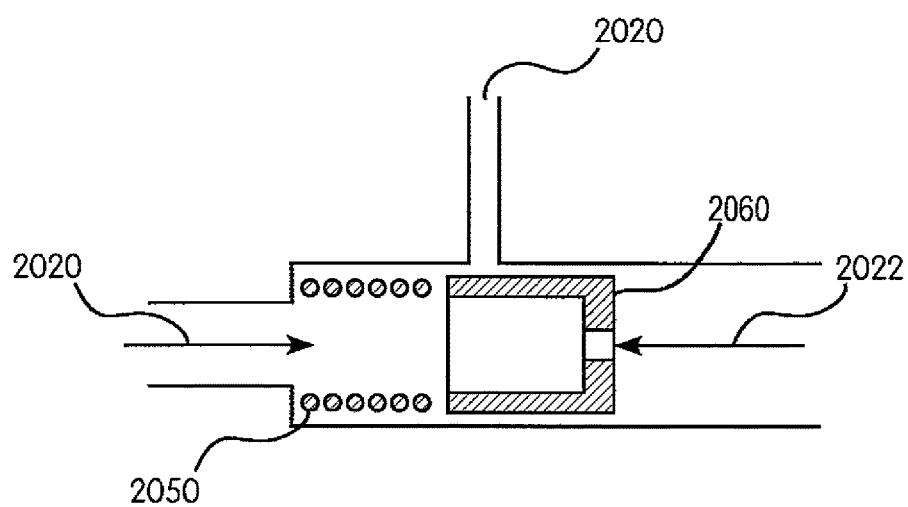

What will next be described, with reference to FIG. 20, is an exemplary spool valve embodiment according to the present invention. FIG. 20(a) depicts the valve in the open position and FIG. 20(b) depicts the valve in the closed position. With reference to FIG. 20(a), there is a saline port 2020, a output port that goes to the patient 2021, and a contrast medium or high pressure input port 2022. There is provided as well a spring 2050 which exerts pressure on a spool 2051, which is a cylinder with a hollowed-out center which is accessed from the high pressure port 2022 via an orifice 2052.

When there is no high pressure on the back circular plane of the spool 2051, the spring 2050 holds it in such manner that the saline port 2020 has a fluid pathway to the patient output port 2021. This is the situation depicted in FIG. 20(*a*). With reference to FIG. 20(*b*), the situation is depicted where there is high pressure fluid flow entering the valve through the high pressure input port 2022, which exerts pressure on the back cylindrical plane 2060 of the spool and pushes it against the spring 2050 such that it moves to the left in the diagram or in the direction of fluid flow, occluding the opening of the saline port 2022, thus protecting it. Therefore, if a low pressure, high-sensitivity transducer can be placed within the protective saline port 2020 such that it can measure the pressure of fluid, and therefore the pressure in the patient when there is no high pressure flow, and when there is high pressure fluid flow at the high pressure input port 2022, the protected leg and therefore the transducer within it are cut off from the fluid flow and the high pressure of the high pressure fluid flow is not exerted on the low-pressure transducer.

Bi-directional Disc Valve

Figure 21A:
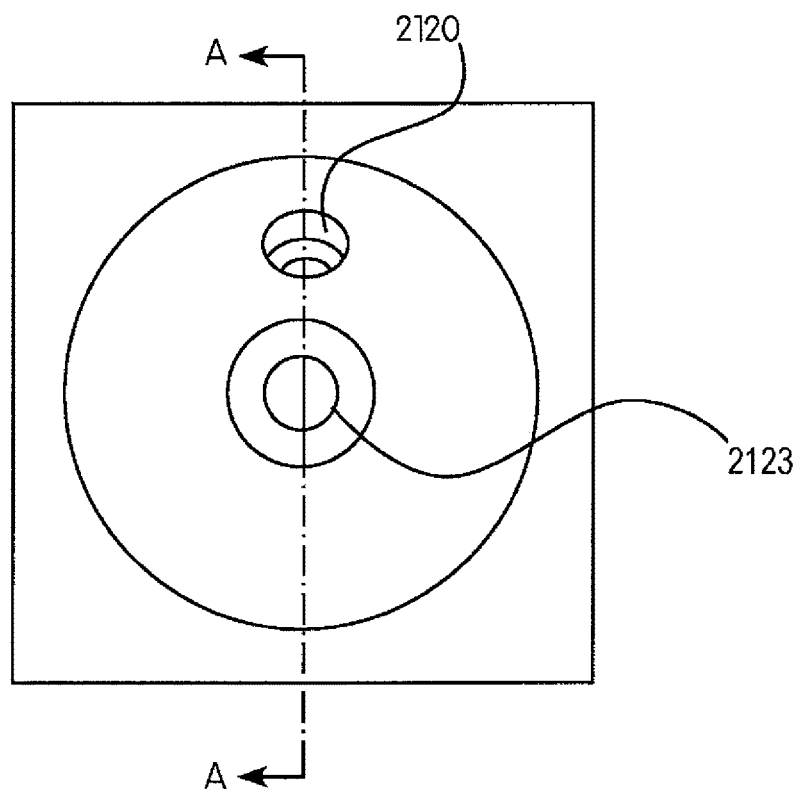
FIGS. 21(a) and 21(b) depict an exemplary bidirectional elastomeric valve according to the present invention.
Figure 21B:
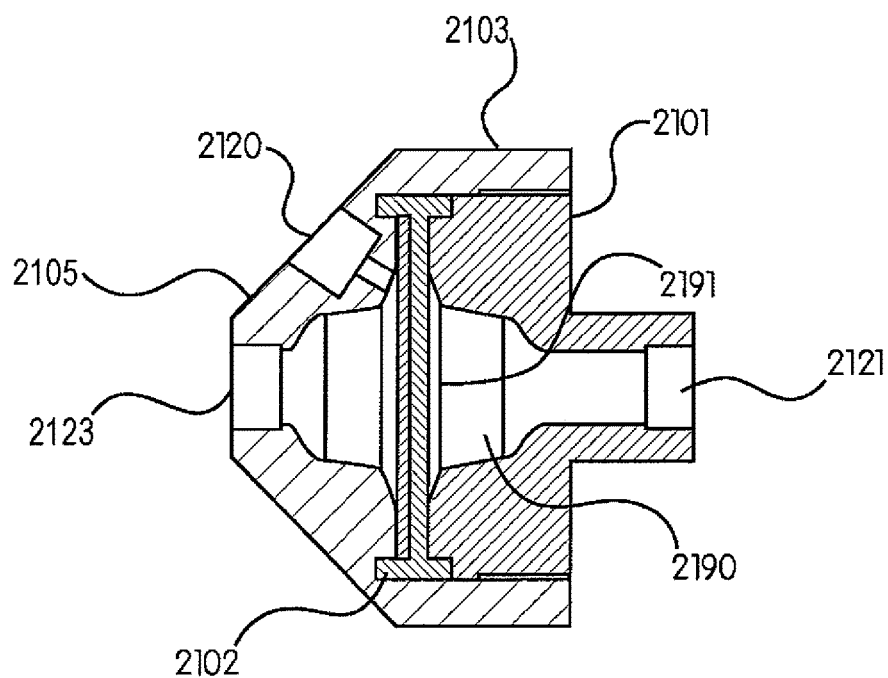

With reference to FIGS. 21(*a*) and 21(*b*), an additional exemplary embodiment of the disc valve is depicted. As can be seen from FIG. 21(*b*), this is a bi-directional high pressure elastomeric valve. Port 1 2121 and Port 3 2123 could either be used as an input or an output for high pressure fluid flow. In the exemplary embodiment depicted in FIG. 21(*b*), the valve disc 2102 is similar to the valve disc used in the prior exemplary unidirectional embodiments discussed, however the shapes of the disc holder 2101 and the valve body 2103 have changed somewhat to become more similar. This is because in order for the flow to be bi-directional there needs to be a cavity on both sides of the valve disc. Thus the two cavities tend to look similar. While saline ports can be provided on both sides, they can only be protected from high pressure flow when the saline port that is used is on the output side of the high pressure flow. For example, with reference to FIG. 21(*b*), the depicted saline Port 2 2120 can only be protected if Port 1 2121 is the input and Port 3 2123 is the output. Although the exemplary embodiment depicted in FIG. 21(*b*) shows an identical angle of displacement of the valve disc under high pressure flow, i.e., 30° off of the vertical in each direction, it is not necessary that these angles be identical, and designers will use variations in the sizes of the cavities on either side of the valve disc as well as the angle of full distention of the valve disc to vary the cracking pressure in each of the forward and backward directions. There are many exemplary uses which such a bi-directional high pressure elastomer valve would have, among them, for example, are using it in the forward direction as the unidirectional valve described above, and then also using it as a high pressure check valve, such that back flow is allowed at a certain high pressure which exceeds the cracking pressure in the backward direction.

It is thus understood that the bi-directional high pressure elastomeric valve depicted in FIGS. 21(*a*) and 21(*b*) will have many uses beyond simply protecting low-pressure transducers or low-pressure systems from high pressure flow in angiographic procedures.

Enhanced HP Transducer (No Valve Protection Required)

Within the objects of the present invention are methods and systems to protect low-pressure systems (such as, for example, those containing low-pressure and high sensitivity, but low over-pressure rated transducers) from high pressure flow. Thus far what has been described are various exemplary embodiments of the valves which are designed to do that. The other side of the coin, however, is to design a transducer with additional apparatus that will protect it from the pressures exerted by high pressure fluid flow, even if it is exposed to such high pressure fluid flow. What is next described with reference to FIGS. 22 through 26 are transducer designs that do just that. Using the transducers, the exemplary embodiments of which are depicted in FIGS. 22 through 26, there is no need to put the transducer in a protected low-pressure line, such as, for example, the saline port as described above in the valve embodiments. Rather, the transducer can be placed within a high pressure line. When high pressure fluid flow is present in the line the transducer will be exposed to that high pressure, but a barrier apparatus will protect the transducer such that the pressure exerted against it is held at certain maximum which is below the overpressure rating for the transducer. When there is low pressure in the line the transducer is free to operate in its full dynamic range and measure, according to its high sensitivity, various intercardiac, intravenous, or interstitial pressures as may be desirous to be measured in a given patient.

Figure 22:
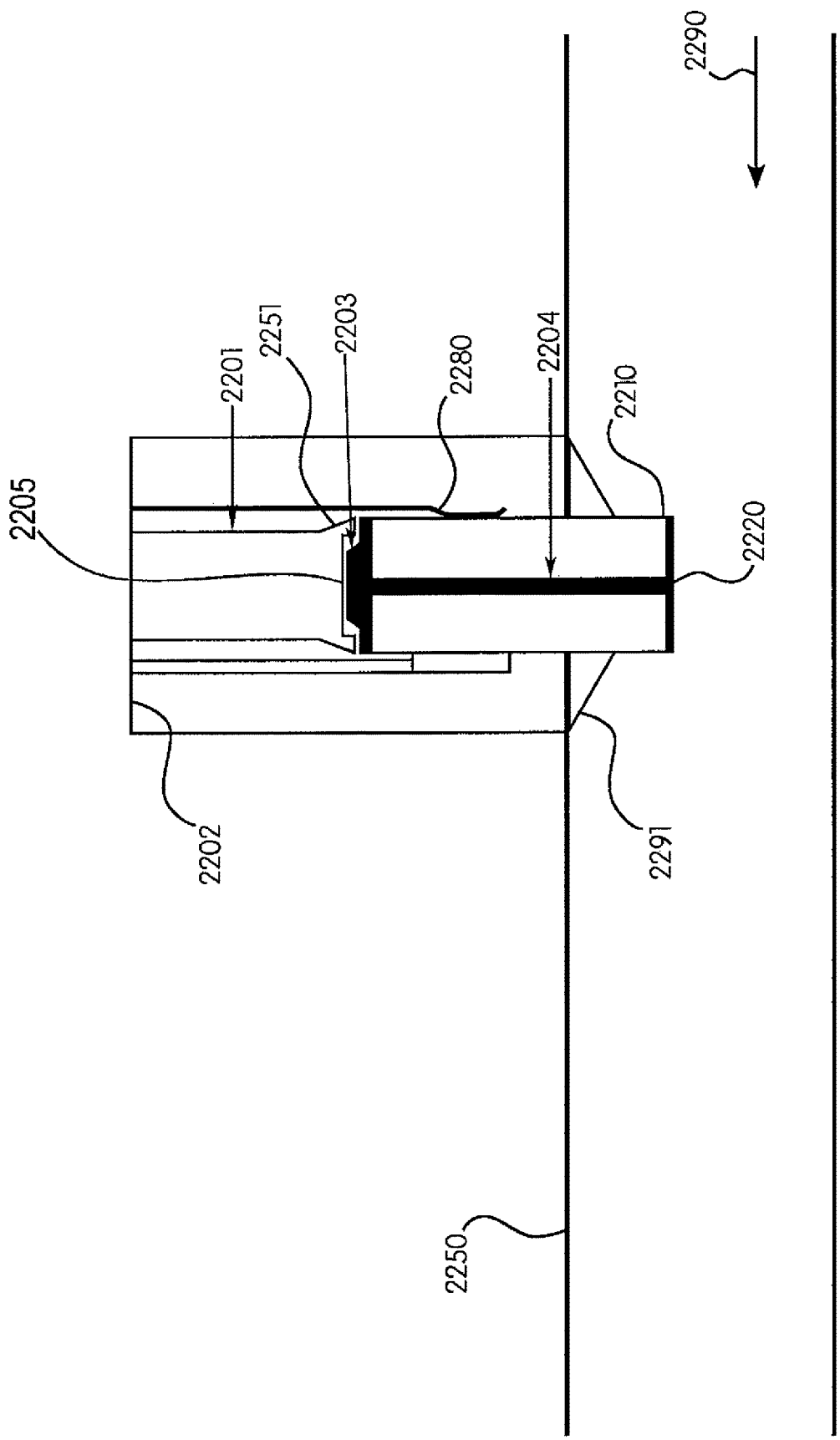
FIG. 22 depicts an exemplary transducer with barrier apparatus according to the present invention.

With reference to FIG. 22, there is provided a transducer 2201 within a transducer housing 2202 and a transducer contact 2203 which impacts upon the transducer 2201 pressing against the impact plane 2205 of the transducer. The transducer contact 2203 is moved ultimately by the membrane contact 2210 which is within a high pressure tubing 2250 and exposed to any high pressure fluid flow, as indicated by the arrow 2290 at the bottom right of the tubing. The fluid pressure is exerted on the transducer contact 2203 via a pressure transmission rod 2204 which is connected to the plane of a membrane 2220 via a membrane contact 2210. Thus, the pressure transmission rod, the membrane contact, the transducer contact and the transducer, are all insulated from actual contact with the fluid for hygienic purposes. The only part having contact with the actual fluid is the membrane 2220. The fluid is not allowed to enter into the transducer housing 2202 by operation of the seal ring 2291, which provides a means to insert the transducer housing into the high pressure tubing but seal it off from any fluid communication therewith.

As can be seen with reference to FIG. 22, a fluid flow in the high pressure tubing will exert pressure on the membrane 2220, which will transmit it to the membrane contact 2210 and by means of a pressure transmission rod 2204 transfer the resultant force to the transducer contact 2203. The transducer contact 2203 will then be pushed in the upward direction, exerting a pressure on the transducer 2201. However, the transducer contact is limited as to how much pressure it can exert against a transducer by means of the transducer contact limiter 2251, which is a ring around the outward perimeter or circumference of the transducer, which serves to stop the transducer contact from any further upward vertical motion. The transducer contact limiter is comprised of any rigid material as may be known in the art. Although it may not be absolutely rigid the transducer contact limiter will have a spring constant which is significantly more rigid than that of the transducer. Thus, in relative terms the transducer contact limiter provides much more rigid resistance to the upward motion of the transducer contact than does the transducer itself. This allows the transducer to measure any pressure between zero and a certain maximum which is governed by the stopping effect that the transducer contact limiter has on the upward motion of the transducer contact. This maximum pressure which can be measured by the transducer will, of course, be set below its overpressure rating by a significant safety margin, as may be chosen by a given designer according to criteria as may be known in the art. In an exemplary embodiment such safety margin will be 20%.

Such a configuration allows the transducer to measure a wide range of pressures in a very sensitive manner within the biological or physiological regime, such as, for example, pressures normally occurring in patients to which the high pressure tubing is connected; however, when there is high pressure flow within the high pressure tubing 2250, such as in angiographic procedures as described above, the pressure reading by the transducer will be capped at the maximum pressure.

Also shown in FIG. 22 is ECG contact 2280, the functionality of which is explained in detail below with reference to FIGS. 25 and 26.

Figure 23:
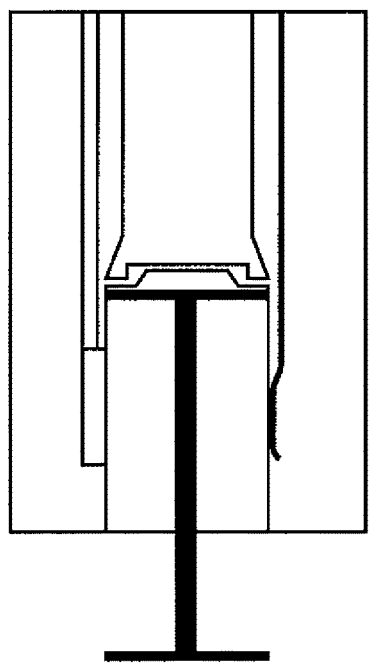
FIG. 23 depicts a non-disposable portion of the exemplary transducer of FIG. 22.

FIG. 23 illustrates the portion of the transducer depicted in FIG. 22 which does not contact the fluid and is a non-disposable multi-use apparatus.

Figure 24:
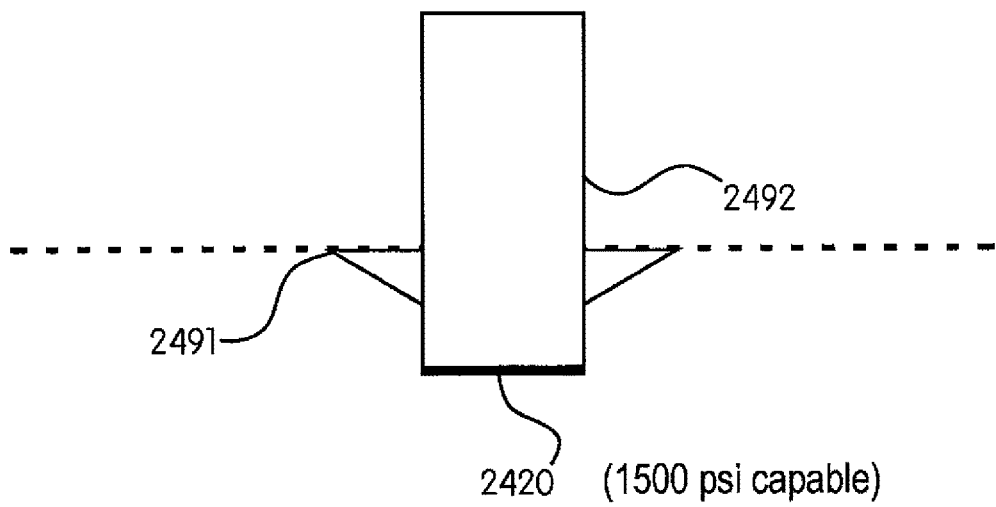
FIG. 24 depicts a disposable portion of the exemplary transducer of FIG. 22.

FIG. 24 depicts the disposable portion of the transducer assembly depicted in FIG. 22, being the membrane 2420, the seal ring 2491, and a stainless steel tube 2492. It is within the hollow of the stainless steel tube that the transducer contact and the transmission rod move up or down, as determined by the pressure exerted against the membrane. As can be seen in the exemplary embodiment of the membrane depicted in FIG. 24, it can withstand pressures up to 1500 psi, which means that it is impervious to fluid flow up to those pressures.

Figure 25:
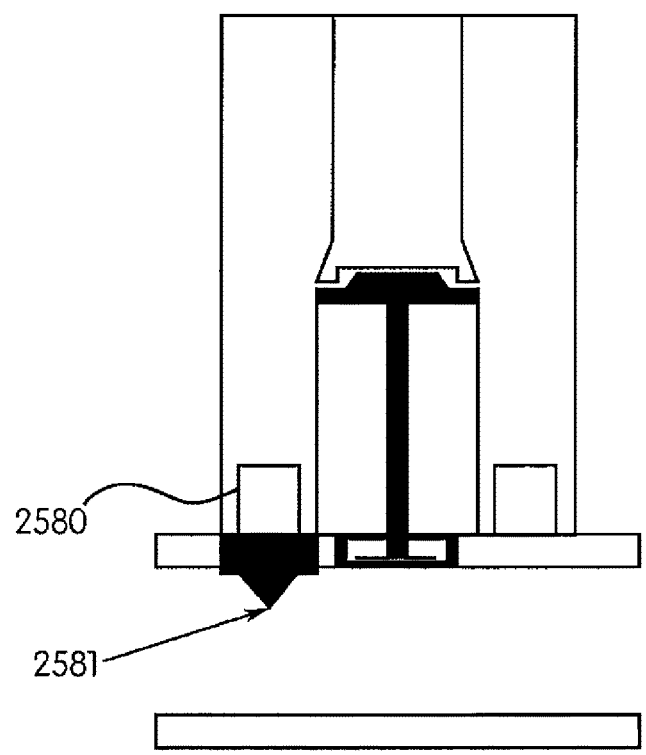
FIGS. 25-26 depict an alternative exemplary transducer with barrier apparatus according to the present invention.
Figure 26:
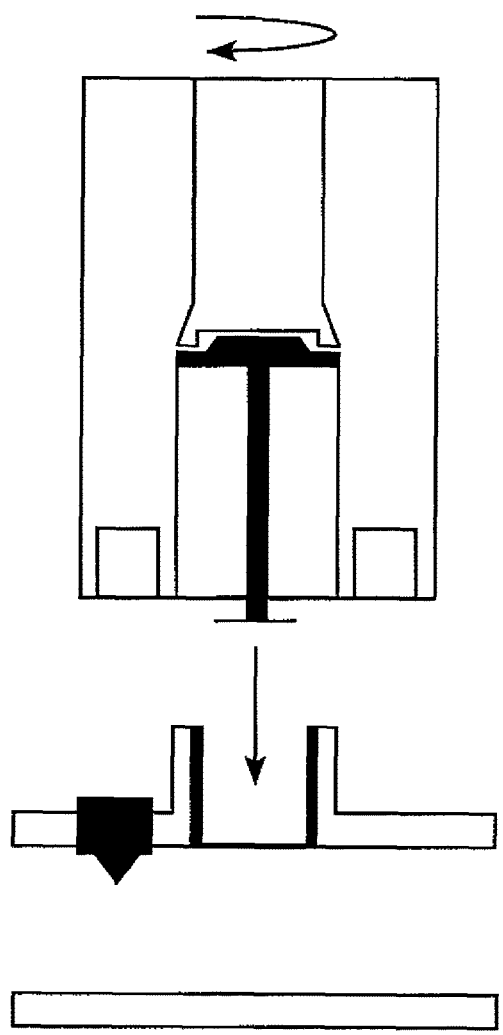

FIGS. 25 and 26 depict an alternative exemplary embodiment of the high pressure transducer. In this embodiment the transducer probe (being the pressure transmission rod in the membrane contact, as depicted in FIG. 22), does not extend downward into the high pressure tubing, but measure pressures at the tubing layer itself. This is done by screwing on the transducer housing as opposed to inserting it within the cavity of the high pressure tubing. The functionality of the alternative exemplary embodiment is equivalent, the only differences between the two exemplary embodiments being the mechanism of insertion or affixation of the transducer, pressure transmission rod, and membrane contact to the high pressure tubing in such manner that it can reliably measure pressures. In the second exemplary embodiment since there is no protrusion into the volume of the tubing, there is no need for the metallic tube 2492 of FIG. 24. Thus, the ECG contact needs a conductive pathway to the fluid in the tube. This is provided by the ECG metal lead 2581, to which the circular ECG Contact 2580 connects.

The ECG contact is utilized in the following manner. During medical procedures, catheters are often inserted into the vasculature to measure pressure, withdraw blood or inject contrast media or other substances. In such instances the lumen of the catheter tubing is generally filled with a conductive liquid, such as, for example, saline, blood or radiographic contrast media.

During certain medical procedures such as, for example, angiography, it is also often desirable to obtain an electrocardiographic measurement of the heart's electrical activity. Such a measurement is usually obtained, for example, from electrodes applied to the patient's skin or from electrodes mounted on the outside of catheters. A minimum of two electrocardiographic electrode attachments to the patient are generally required and the voltage potential between the electrodes (either singly or in groups) is recorded over time. These measurements allow monitoring of the patient's condition as well as diagnosis of specific heart abnormalities, such as, for example, such as lack of blood flow.

In the exemplary embodiment depicted in FIGS. 25 and 26, the electrocardiographic (ECG) electrodes from the heart can be obtained through the conductive fluid in the lumen of the catheter in the patient. The other (return path) electrode, or combination of electrodes, can be obtained from surface electrodes attached to the patient's skin or from electrodes attached to the side of the catheter within the patient. Alternatively, two electrode leads could be obtained from the lumens of a catheter with two or more lumens filled with a conductive substance.

The sensing of at least one ECG electrode from the catheter lumen would allow easier ECG measurements for patients undergoing such medical procedures because it would simplify or eliminate the need for skin electrodes. It would also allow a recording of the intravascular ECG, which may have diagnostic importance or be useful for other purposes as may be known in the art.

Shuttle Valve with Manual Override

Figure 27A:
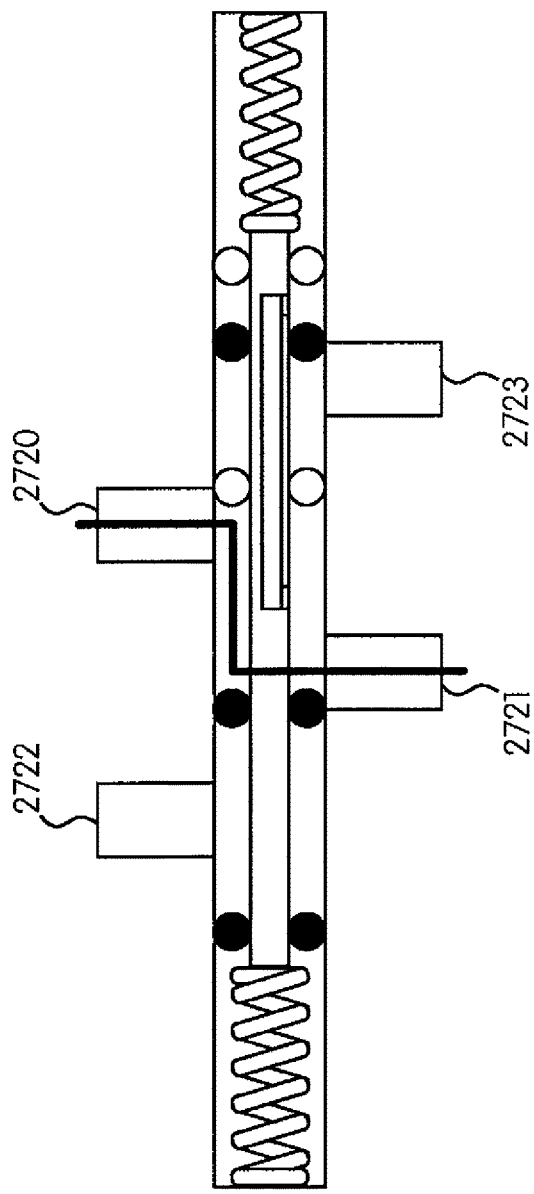
FIGS. 27(a)-27(c) depict an exemplary embodiment of an automatic shuttle valve with manual override.
Figure 27B:
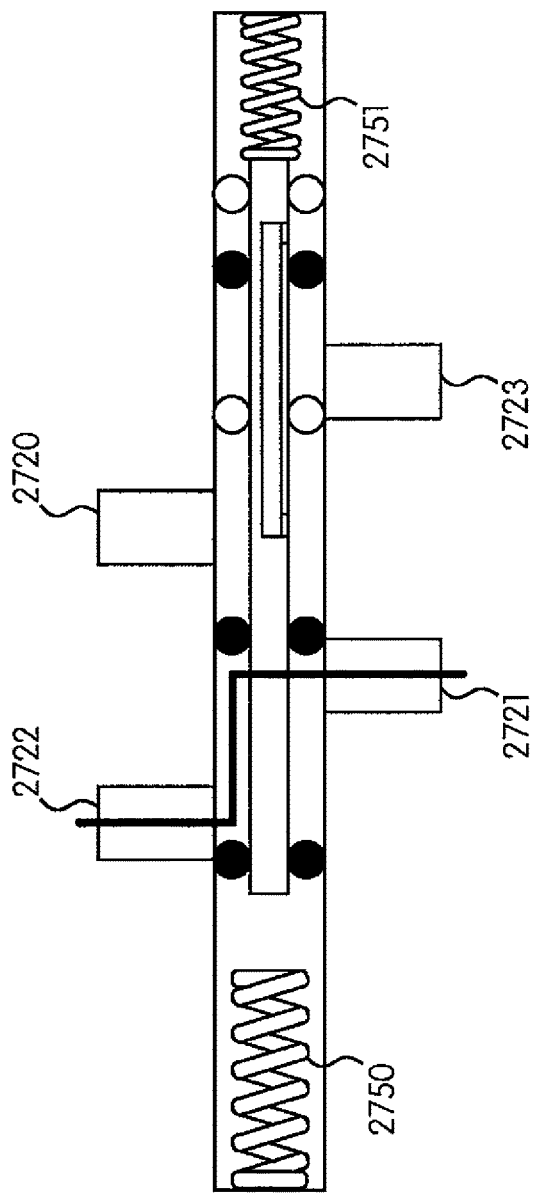
Figure 27C:
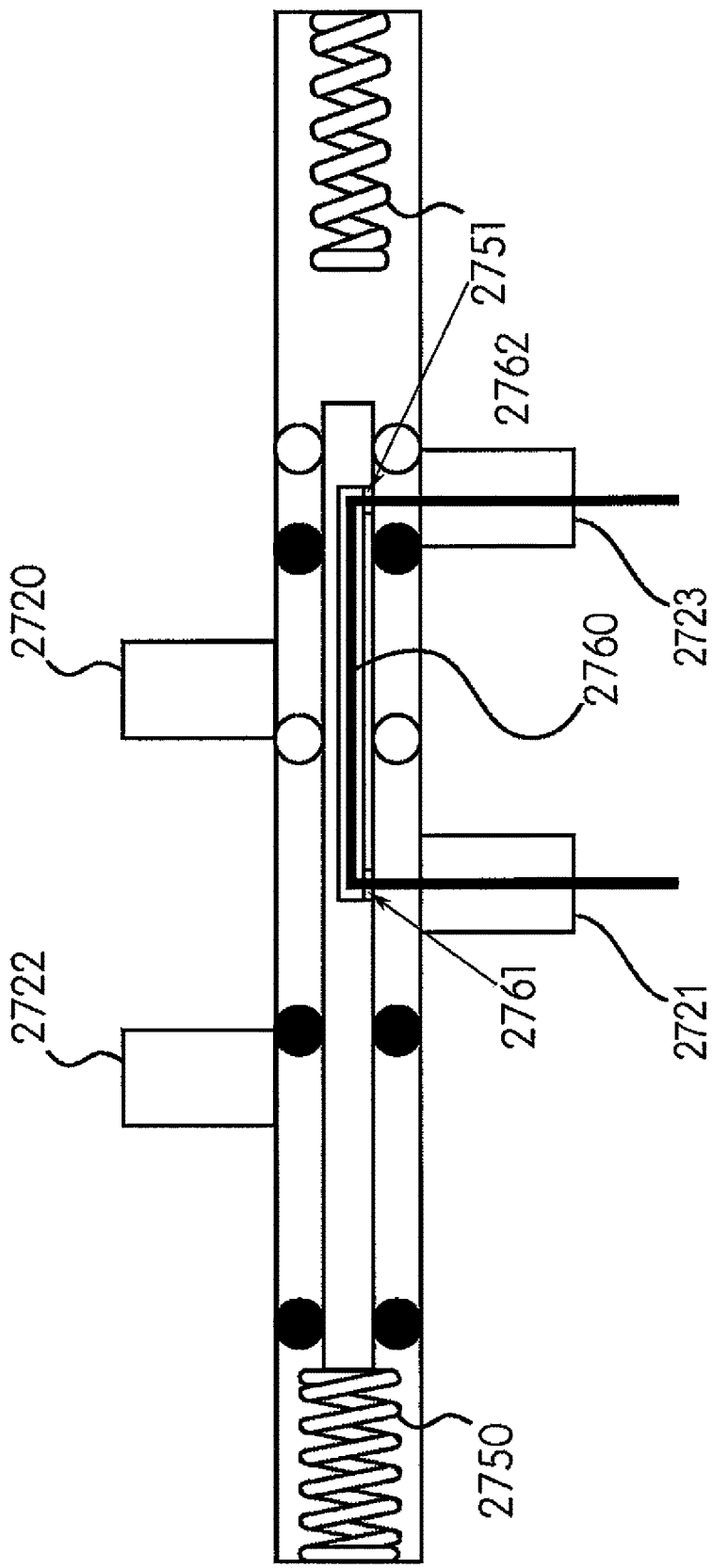

FIG. 27(*a*) through 27(*c*) depict an exemplary embodiment of a shuttle valve with manual override. In general, in the exemplary embodiments of valves discussed so far, there have been two position/three way valves, which direct either saline or contrast to a single port connected to the patient. In such systems, it is further required to have a three position/three way stopcock distal from the valve to aspirate fluid from and administer fluid to the same patient connection. This increases cost and complexity. The exemplary embodiment shuttle valve depicted in FIG. 27 merges these two functions in one valve by adding an additional sample/aspiration port 2723, as shall next be described. The exemplary embodiment of FIG. 27 also allows existing two position/three way valves to be located at the extreme distal end of a disposable set, which may in fact increase the accuracy and fidelity of biological pressure waveforms by substituting a lumen filled with contrast with one filled with less viscous saline. Moreover, a push-button style valve is generally easier to actuate than a similar rotary style valve.

In an exemplary embodiment of the shuttle valve shown in FIG. 27, the ports are configured in parallel. This facilitates the use of a side-by-side dual lumen tube. With reference to FIG. 27(*a*), there is depicted the normal state of the valve where the saline port 2720 has an open fluid communication pathway with the patient output port 2721. This figure also depicts the contrast port 2722 as described above, and an additional port unique to this embodiment which is the sample/aspiration port 2723. With reference to FIG. 27(*b*), the shuttle has moved rightward within the figure, according to the following process. The spring on the left, shown with the larger windings, 2750 has a higher spring constant. The spring on the right 2751 has a lower spring constant. In normal operation as depicted in FIG. 27(*a*), the spring with lower force constant biases the shuttle 2750 against the spring with the higher force constant. During an injection, however, fluid pressure from the flow into the contrast port 2722 shifts the shuttle against the spring with the lower force constant 2751 closing up the saline port 2720 to the patient port 2721 and opening the contrast port 2722 to the patient port 2721. Once the injection is complete, the low force constant spring 2751 once again biases the shuttle toward the high force constant spring 2750, thus reopening the connection between the patient 2721 and saline 2720 ports while closing the connection between the contrast 2722 and patient 2721 ports.

Additionally, according to the exemplary embodiment depicted in FIG. 27(*a*), when desired the shuttle may be manually biased further towards the high force constant spring 2750 which opens a connection between the sample aspiration port 2723 and the patient port 2721 by means of a bypass connection 2760 from bypass inlet 2761 to bypass outlet 2762 between the patient 2721 and sample 2723 ports. This situation is depicted in FIG. 27(*c*). This opening of a connection between the sample/aspiration 2723 and patient 2721 ports closes the other two ports, namely the contrast port 2722 and the saline port 2720. Such a configuration allows for a sample aspiration, blood aspiration, or the administration of medications. The manual biasing of spring 2750 can be implemented and released via a push button, or such other device as may be known in the art.

Figure 28A:
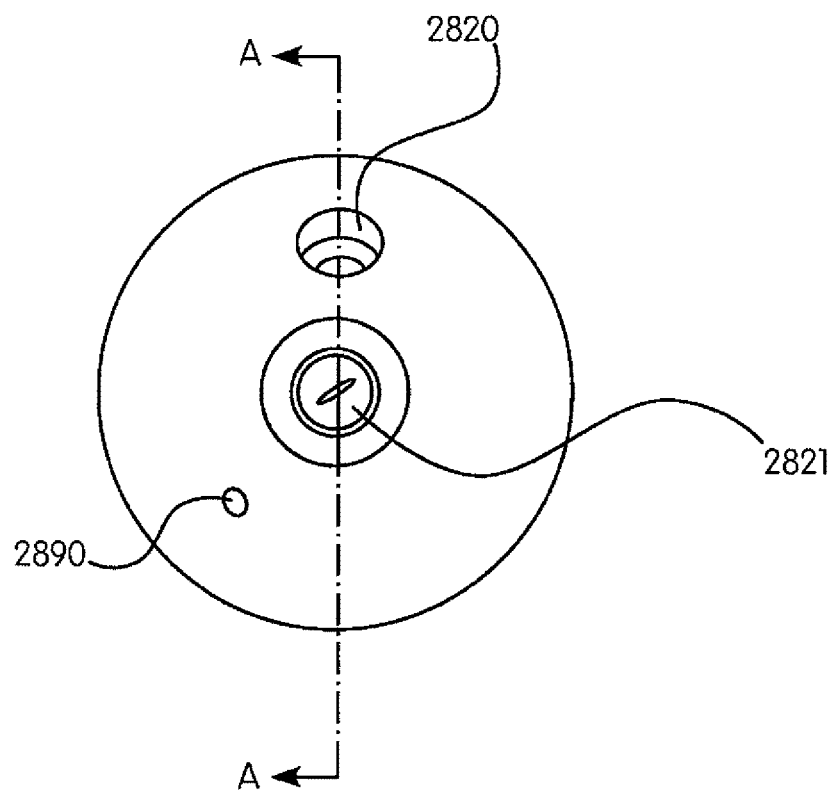
FIGS. 28(a)-28(c) depict an exemplary disc valve according to the present invention with a built-in seat for a low pressure transducer.
Figure 28B:
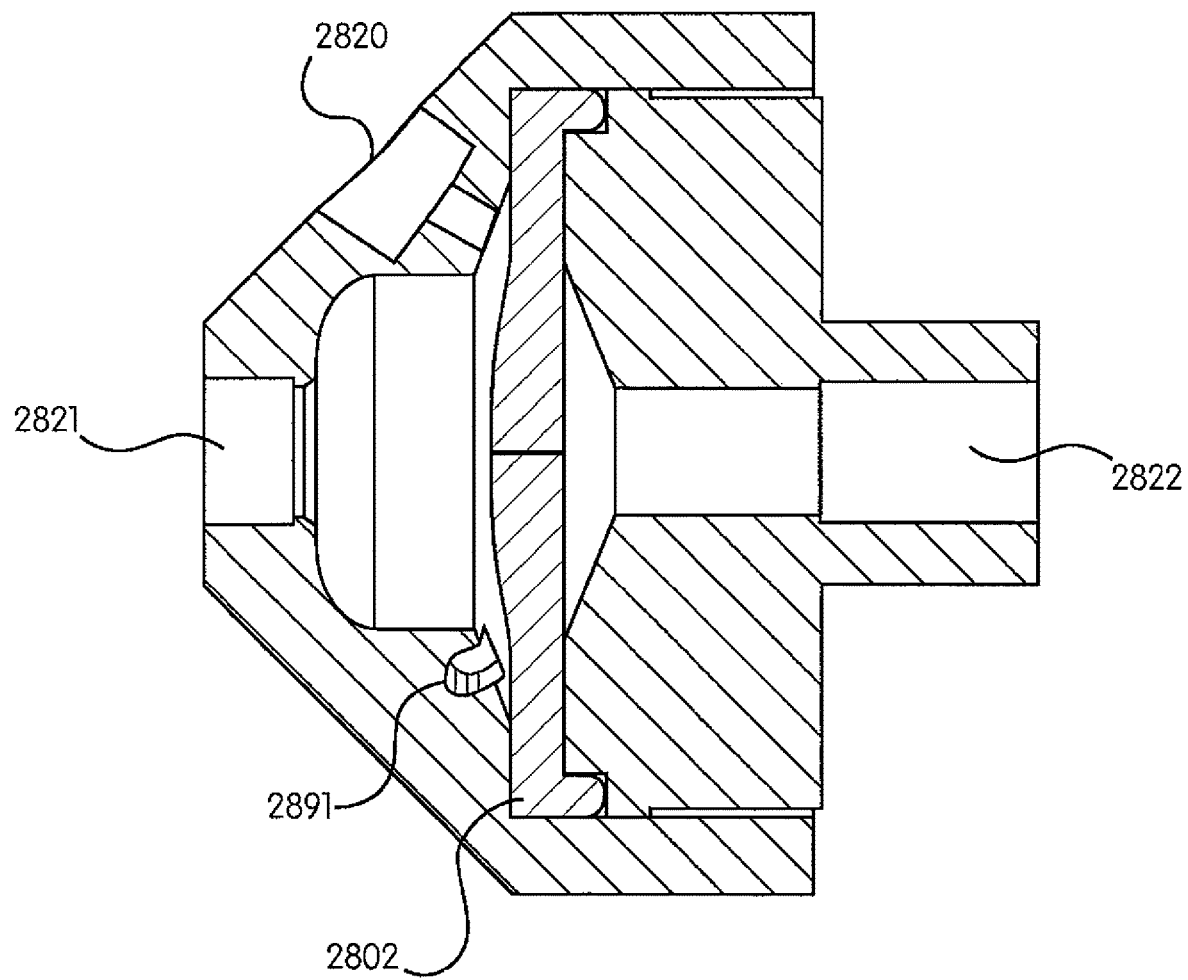
Figure 28C:
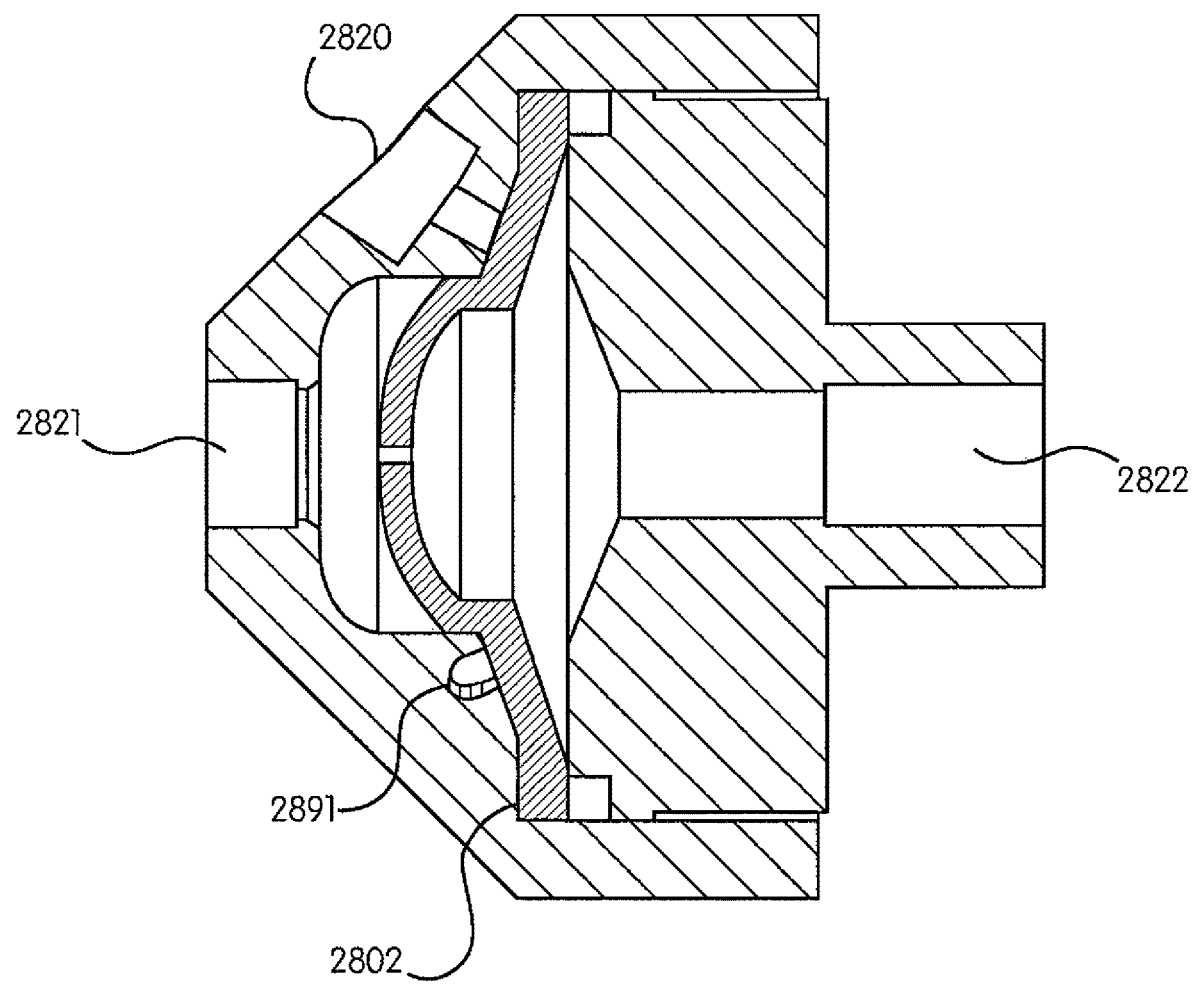

FIGS. 28(*a*) through 29(*c*) depict an alternate exemplary embodiment of a disc valve. In this exemplary embodiment, location for a transducer is provided within the valve body itself. With reference to FIG. 28(*a*), there is provided an output port 2821, a saline port 2820, and a transducer lead port 2890, through which electric leads running out of a transducer can be run. FIG. 28(*b*) depicts a cross section of FIG. 28(*a*), depicting a high pressure input 2822, an output port 2821, a saline port 2820, and an exemplary location for a transducer 2891. Both the saline port and the transducer at location 2891 are sealed off from any high pressure flow by disc member 2802, here shown in the normal position. FIG. 28(*c*) depicts the disc in the open position, as when high pressure flow enters via high pressure input port 2822.

The present invention has been described in connection with exemplary embodiments and exemplary preferred embodiments and implementations, as examples only. It will be understood by those having ordinary skill in the pertinent art that modifications to any of the embodiments or preferred embodiments may be easily made without materially departing from the scope and spirit of the present invention as defined by the appended claims.

What is claimed:

1. A method comprising:
providing, by a fluid injection system, a fluid valve comprising a first inlet port, a second inlet port, an outlet port, and a valve body comprising an elastomeric component, wherein the outlet port is substantially aligned with the first inlet port, wherein the valve body defines a first fluid path from the first inlet port to the outlet port, and wherein the valve body further defines a second fluid path from the second inlet port to the outlet port;
allowing, by the elastomeric component, the second fluid path to be open when there is substantially no fluid flow through the valve body; and
closing the second fluid path, by the elastomeric component, when a fluid pressure at the first inlet port exceeds a defined pressure.

2. The method of claim 1, further comprising:
providing, by the fluid injection system, first tubing from the first inlet port of the fluid valve to a first fluid reservoir; and
providing, by the fluid injection system, second tubing from the second inlet port of the fluid valve to a second fluid reservoir.

3. The method of claim 2,
wherein the first fluid reservoir contains contrast media, and
wherein the second fluid reservoir contains saline.

4. The method of claim 1, wherein allowing the second fluid path to be open comprises allowing, by the elastomeric component, the second fluid path to be open when the fluid pressure at the first inlet port is less than the defined pressure.

5. The method of claim 1, wherein when the fluid pressure at the first inlet port exceeds the defined pressure, the second fluid path is closed due to movement of the elastomeric component.

6. The method of claim 1, wherein when the fluid pressure at the first inlet port exceeds the defined pressure, the second fluid path is closed due to a change in shape of the elastomeric component.

7. The method of claim 6, wherein the first fluid path is open when the fluid pressure at the first inlet port exceeds the defined pressure.

8. The method of claim 1,
wherein the first inlet port of the fluid valve is aligned on a first axis, and
wherein the second inlet port of the fluid valve is aligned on a second axis, the second axis being substantially different than the first axis.

9. The method of claim 1, wherein the first fluid path comprises a unidirectional fluid path from the first inlet port to the outlet port.

10. A method comprising:
providing, by a fluid injection system, a fluid valve comprising a first inlet port aligned on a first axis, a second inlet port aligned on a second axis substantially different than the first axis, an outlet port, and a valve body comprising an elastomeric component, wherein the valve body defines a first fluid path from the first inlet port to the outlet port, and wherein the valve body further defines a second fluid path from the second inlet port to the outlet port;
allowing, by the elastomeric component, the second fluid path to be open when there is substantially no fluid flow through the valve body; and
closing the second fluid path, by the elastomeric component, when a fluid pressure at the first inlet port exceeds a defined pressure.

11. The method of claim 10, further comprising:
providing, by the fluid injection system, first tubing from the first inlet port of the fluid valve to a first fluid reservoir; and
providing, by the fluid injection system, second tubing from the second inlet port of the fluid valve to a second fluid reservoir.

12. The method of claim 10, wherein allowing the second fluid path to be open comprises allowing, by the elastomeric component, the second fluid path to be open when the fluid pressure at the first inlet port is less than the defined pressure.

13. The method of claim 10, wherein when the fluid pressure at the first inlet port exceeds the defined pressure, the second fluid path is closed due to movement of the elastomeric component.

14. The method of claim 10, wherein when the fluid pressure at the first inlet port exceeds the defined pressure, the second fluid path is closed due to a change in shape of the elastomeric component.

15. The method of claim 14, wherein the first fluid path is open when the fluid pressure at the first inlet port exceeds the defined pressure.

16. The method of claim 10, wherein the first fluid path comprises a unidirectional fluid path from the first inlet port to the outlet port.

17. The method of claim 10, wherein the second inlet port is located in a taper at an angle from a plane that is normal to a direction of fluid flow from the first inlet port.

18. A fluid valve comprising:
a first inlet port;
a second inlet port;
an outlet port substantially aligned with the first inlet port;
a valve body defining a first fluid path from the first inlet port to the outlet port, the valve body further defining a second fluid path from the second inlet port to the outlet port;
means for allowing the second fluid path to be open when there is substantially no fluid flow through the valve body, and for closing the second fluid path when a fluid pressure at the first inlet port exceeds a defined pressure.

19. The fluid valve of claim 18, wherein the first fluid path is open when the fluid pressure at the first inlet port exceeds the defined pressure.

20. The fluid valve of claim 18,
wherein the first inlet port of the fluid valve is aligned on a first axis, and
wherein the second inlet port of the fluid valve is aligned on a second axis, the second axis being substantially different than the first axis.

21. A fluid valve comprising:
a first inlet port aligned on a first axis;
a second inlet port aligned on a second axis, the second axis being substantially different than the first axis;
an outlet port;
a valve body defining a first fluid path from the first inlet port to the outlet port, the valve body further defining a second fluid path from the second inlet port to the outlet port;
means for allowing the second fluid path to be open when there is substantially no fluid flow through the valve body, and for closing the second fluid path when a fluid pressure at the first inlet port exceeds a defined pressure.

22. The fluid valve of claim 21, wherein the first fluid path is open when the fluid pressure at the first inlet port exceeds the defined pressure.

23. The fluid valve of claim 21, wherein the second inlet port is located in a taper at an angle from a plane that is normal to a direction of fluid flow from the first inlet port.

\* \* \* \* \*